US006894022B1

(12) United States Patent
Hubbell et al.

(10) Patent No.: US 6,894,022 B1
(45) Date of Patent: May 17, 2005

(54) GROWTH FACTOR MODIFIED PROTEIN MATRICES FOR TISSUE ENGINEERING

(75) Inventors: Jeffrey A. Hubbell, Zumikon (CH); Jason C. Schense, Zurich (CH); Shelly E. Sakiyama-Elbert, Zurich (CH)

(73) Assignees: Eidgenossische Technische Hochschule Zurich, Zurich (CH); Universitat Zurich, Zurich (CH)

( * ) Notice: Subject to any disclaimer, the term of this patent is extended or adjusted under 35 U.S.C. 154(b) by 0 days.

(21) Appl. No.: 09/563,760

(22) Filed: May 1, 2000

Related U.S. Application Data

(63) Continuation-in-part of application No. 09/141,153, filed on Aug. 27, 1998, now abandoned.

(51) Int. Cl.[7] .............................................. A61K 31/727

(52) U.S. Cl. ........................... 514/2; 530/300; 530/350; 435/7.1; 435/7.6; 435/7.8; 435/68.1; 435/69.4; 435/70.1; 514/56

(58) Field of Search ................................. 530/350, 300; 435/7.1, 7.6, 7.8, 68.1, 69.4, 70.1; 514/2

(56) References Cited

U.S. PATENT DOCUMENTS

| | | | |
|---|---|---|---|
| 4,613,665 A | | 9/1986 | Larm |
| 4,810,784 A | | 3/1989 | Larm |
| 5,100,668 A | | 3/1992 | Edelman |
| 5,171,670 A | | 12/1992 | Kronenberg et al. |
| 5,202,247 A | | 4/1993 | Kilburn |
| 5,504,001 A | | 4/1996 | Foster |
| 5,529,986 A | * | 6/1996 | Larsson et al. ............... 514/54 |
| 5,561,982 A | | 10/1996 | Tunkel et al. |
| 5,582,862 A | * | 12/1996 | Reed ....................... 424/145.1 |
| 5,641,670 A | | 6/1997 | Treco et al. |
| 5,693,341 A | | 12/1997 | Schroeder et al. |
| 5,773,577 A | * | 6/1998 | Cappello .................... 530/350 |
| 5,840,837 A | | 11/1998 | Krstenansky et al. |
| 5,874,308 A | | 2/1999 | Kilburn et al. |
| 6,331,422 B1 | * | 12/2001 | Hubbell et al. ............. 435/193 |
| 6,468,731 B1 | * | 10/2002 | Hubbell et al. ............... 435/2 |

FOREIGN PATENT DOCUMENTS

| | | |
|---|---|---|
| DE | 200 10 297 | 8/2000 |
| WO | WO 92/02620 A1 | 2/1992 |
| WO | WO 95/23611 * | 9/1995 |
| WO | WO 00/64481 A | 11/2000 |

OTHER PUBLICATIONS

Jeong, J.–M. et al. (1995) The fibronectin–binding domain of transglutaminase. J. Biol. Chem. vol. 270, pp. 5654–5658.*
Yamada, K. M. et al. (1980) Characterization of fibronectin interactions with glycosaminoglycans and identification of active proteolytic fragments. J. Biol. Chem. vol. 255, pp. 6055–6063.*
Monsonego, A. et al. (1998) Factor XIIIa as a nerve–associated transglutaminase. FASEB J. vol. 12, pp. 1163–1167.*
Jyon, M. et al. (1997) The interaction of the transforming growth factor–betas with heparin/heparan sulfate is isoform–specific. J BIol Chem. vol. 272, pp. 18000–18006.*
Rogers, et al., "Neuron–specific interactions with two neurite–promoting fragments of fibronectin," *J. Neurosci.* 5(2):369–78 (1985).
Sakiyama, et al., "Incorporation of heparin–binding peptides into fibrin gets enhances neurite extension: an example of designer matrices in tissue engineering," *FASEB. J.* 13(15):2214–24 (1999).
Sakiyama–Elbert, et al., "Development of fibrin derivatives for controlled release of heparin–binding growth factors," *J. Controlled Release* 65(3):389–402 (2000).
Schense, et al., "Cross–linking exogenous bifunctional peptides into fibrin gels with factor XIIIa," *Bioconjug. Chem.* 10(1):75–81 (1999).
Seibel, et al., "Transfection of mitochondria: strategy towards a gene therapy of mitochondrial DNA disease," *Nucleic Acids Res.* 23(1):10–7 (1995).
Sellke, et al., "Basic FGF enhances endothelium–dependent relaxation of the collateral–perfused coronary microcirculation," *Am. J. Physiol.* 267(4 pt 2):H1303–11 (1994).
Smith, et al., "Rapid identification of highly active and selective substrates for stromelysin and matrilysin using bacteriophage peptide display libraries," *J. Biol. Chem.* 270(12):6440–9 (1995).
Spillman, et al., "Defining the interleukin–B–binding domain of heparan sulfate," *J. Biol. Chem.* 273(25):15487–93 (1998).
Steffen, et al., "Characterization of cell–associated and soluble forms of connective tissue growth factor (CTGF) produced by libroblast cell sin vitro," *Growth Factors* 15(3):199–213 (1998).
Giannelli, et al., "Transforming growth factor–beta 1 triggers hepatocellular carcinoma invasiveness via alpha3beta 1 integrin," *Am. J. Pathol.* 161(1):183–193 (2002).
Ludbrook, et al., "The integrin alphavbeta3 is a receptor for the latency–associated peptides of transforming growth factors beta1 and beta 3," *Biochem. J.* 389(2): 311–318 (2003).
Nesti, et al., "TGF–beta 1 calcium signaling increases alpha5 integrin expression in ostecblasts," *J. Orthop. Res.* 20(5): 1042–1049 (2002).

(Continued)

*Primary Examiner*—Karen Cochrane Carlson
*Assistant Examiner*—Samuel Wei Liu
(74) *Attorney, Agent, or Firm*—Pabst Patent Group LLP

(57) ABSTRACT

Proteins are incorporated into protein or polysaccharide matrices for use in tissue repair, regeneration and/or remodeling, and/or drug delivery. The proteins can be incorporated so that they are released by degradation of the matrix, enzymatic action, and/or diffusion. In one embodiment, a fusion protein, which contains a crosslinking region, such as a factor XIIIa substrate, and a native protein sequence, such as a bioactive factor, is constructed. Degradable linkages may be included between the crosslinking region and the bioactive factor.

6 Claims, 4 Drawing Sheets

OTHER PUBLICATIONS

Rout, et al., "Transforming growth factor–beta1 modulates expression of adhesion and cytoskeletal proteins in human peritoneal fibroblasts," *Fertil. Steril.* 78(1):154–161 (2002).

Swiss–Prot Primary Accession No. PO2751, Entry name FINC_HUMAN (1966).

Swiss–Prot Primary Accession NO. PO1137, Entry name TGF1_HUMAN (1986).

Besson, et al., "Synthetic peptide substrates for a conductimetric assay of Pseudomonas aeruginosa elastase," *Anal. Biochem.* 237(2):216–23 (1996).

Borrajo, et al., "Derivatized Cyclodextrins as peptidometics: Influence on Neurite Growth," *Bioorganic and Medicinal Chemistry Letters* 7:1185–90 (1997).

Coombs, et al. "Directing sequence–specific proteolysis to new targets. The influence of loop size and target sequence on selective proteolysis by tissue–type plasminogen activator and urokinase–type plasminogen activator," *J. Biol. Chem.* 273(8):4323–8 (1998).

Dimilla, et al., "Mathematical model for the effects of adhesion and mechanics on cell migration speed," *Biophys. J.* 60(1):15–37 (1991).

Dinbergs, et al., "Cellular response to transforming growth factor–beta1 and basic fibroblast growth factor depends on release kinetics and extracellular matrix interactions," *J. Biol. Chem.* 271(47):29822–9 (1996).

Edelman, et al., "Basic fibroblast growth factor enhances the coupling of intimal hyperplasia and proliferation of vase vasorum in injured rat arteries," *J. Clin. Invest.* 89(2):465–73 (1992).

Edelman, et al., "Controlled and modulated release of basic fibroblast growth factor," *Biomaterials.* 12(7):619–26 (1991).

Edelman, et al., "Perivascular and intravenous administration of basic fibroblast growth factor: vascular and solid organ deposition," *Proc. Natl. Acad. Sci. U. S. A.* 90(4):1513–7 (1993).

Edgar, et al., "The heparin–binding domain of laminin is responsible for its effects of neurite outgrowth and neuronal survival," *EMBO J.* 3(7):1463–8 (1984).

Götz, et al., "Neurotrophin–6 is a new member of the nerve growth factor family," *Nature* 372(6503):266–9 (1994).

Grainger, et al., "Poly(dimethylsiloxane)–poly(ethylene oxide)–heparin block copolymers. I. Synthesis and characterization," *J. Biomed. Mater. Res.* 22(3):231–49 (1988).

Harada, et al., "Basic fibroblast growth factor improves myocardial function in chronically ischemica porcine hearts," *J. Clin. Invest.* 94(2):623–30 (1994).

Hata, et al., "Binding of lipoprotein lipase to heparin. Identification of five critical residues in two distinct segments of the amino–terminal domain," *J. Biol. Chem.* 268(12):8447–57 (1993).

Haugen, et al, "Central and peripheral neurite outgrowth differs in preference for heparin–binding versus integrin–binding sequences," *J. Neurosci.* 12(6):2034–42 (1992).

Herbert, et al., "Effects of fibinolysis on neurite growth from dorsal root ganglia cultured in two– and three– dimensional fibrin gels," *J. Comp. Neurol.* 365(3):380–91 (1996).

Herbert, et al., "Effects of fibrin micromorphology on neurite growth from dorsal root ganglia cultured in three– dimensional fibrin gels," *J. Biomed. Mater. Res.* 40(4):551–9 (1998).

Kallapur, et al, "The neural cell adhesion molecular (NCAM) heparin binding domain binds to cell surface heparan sulfate proteoglycans," *J. Neurosci. Res.* 33(4):538–48 (1992).

Kaneda, et al., "Midkine, a heparin–binding growth/differentiation factor, exhibits nerve cell adhesion and guidance activity for neurite outgrowth in vitro," *J. Biochem.* 119(6):1150–6 (1996).

Kiguchi, et al., "Altered expression of epidermal growth factor receptor ligands in tumor promoter–treated mouse epidermis and in primary mouse skin tumors induced by an initiation–promotion protocol," *Mol. Carcinog.* 22(2):73–83 (1998).

Kinosaki, et al., "Identification of heparin–binding stretches of a naturally occurring deleted variant of hepatocyte growth factor (dHGF)," *Biochim. Biophys. Acta.* 1384(1):93–102 (1998).

Kleinman, et al., "The laminins: a family of basement membrane glycoproteins important in cell differentiation and tumor metastases," *Vitam. Horm.* 47:161–86 (1993).

Lopez, et al., "Basic fibroblast growth factor in a porcine model of chronic myocardial ischemia: a comparison of angiographic, echocardiographic and coronary flow parameters," *J. Pharmacol. Exp. Ther.* 282(1):385–90 (1997).

Lopez, et al., "Local perivascular administration of basic fibroblast growth factor: drug delivery and toxicological evaluation," *Drug Metab. Dispos.* 24(8):922–4 (1996).

Martin & Timpl, "Laminin and other basement membrane components," *Annu. Rev. Cell. Biol.* 3:57–85 (1987).

Massia, et al., "An RGD spacing of 440 nm is sufficient for integrin alpha V beta 3–mediated fibroblast spreading and 140 nm for local contact and stress fiber formation," *J. Cell. Biol.* 114(5):1089–100 (1991).

McCaffrey; et al., "Transforming growth factor–beta 1 is a heparin–binding protein: identification of putative heparin–binding regions and isolation of heparins with varying affinity for TGF–beta 1," *J. Cell. Physiol.* 152(2):430–40 (1992).

Netzel–Arnett, et al., "Sequence specificities of human fibroblast and neutrophil collagenases," *J. Biol. Chem.* 266(11):6747–55 (1991).

Nolo, et al., "Developmentally regulated neurite outgrowth response from dorsal root ganglion neurons to heparin–binding growth–associated molecule (HB–GAM) and the expression of HB–GAM in the targets of the developing dorsal root ganglion neurites," *Eur. J. Neurosci.* 8(8):1658–65 (1996).

Presta, et al., "Structure–function relationship of basic fibroblast growth factor: site–directed mutagenesis of a putative heparin–binding and receptor–binding region," *Biochem. Biophys. Res. Commun.* 185(3):1098–107 (1992).

Rixon, et al., "Do the non–catalytic polysaccharide–binding domains and linker regions enhance the biobleaching properties of modular xylanases?" *Appl. Microbiol. Biotechnol.* 46(5–6):514–20 (1996).

Studier, et al., "Use of T7 RNA polymerase to direct expression of cloned genes," *Methods Enzymol.* 185:60–89 (1990).

Takagi & Doolittle, "Amino acid sequences studies on the alpha chain of human fibrinogen. Location of four plasmin attack points and a covalent cross–linking site," *Biochemistry* 14(23):5149–56 (1975).

Takagi, et al., "Amino acid sequence studies on the alpha chain of human fibrinogen. Location of four plasmin attack–points and a covalent–cross–linking site," *Biochemistry* 14(23):5149–56 (1975).

Tashiro, et al., "A synthetic peptide containing the IKVAV sequence from the A chain of laminin mediates cell attachment, migration, and neurite outgrowth," *J. Biol. Chem.* 264(27):16174–82 (1989).

Tessler, et al., "Heparin modulates the interaction of VEGF 165 with soluble and cell associated fik–1 receptors," *J. Biol. Chem.* 269(17):12456–61 (1994).

Tyler–Cross, et al., "Heparin binding domain peptides of antithrombin III: analysis by isothermal titration calorimetry and circular dichroism spectroscopy," *Protein Sci.* 3(4):620–7 (1994).

Yamada, "Adhesive recognition sequences," *J. Biol. Chem.* 266(20):12809–12 (1991).

Yanish–Perron, et al., "Improved M13 phage cloning vectors and host strains: nucleotide sequences of the M13mp18 and pUC19 vectors," *Gene.* 33(1):103–19 (1985).

Zucker & Katz, "Platelet factor 4: production, structure, and physiologic and immunologic action," *Proc. Soc. Exp. Biol. Med.* 198(2):693–702 (1991).

\* cited by examiner

US 6,894,022 B1

GROWTH FACTOR MODIFIED PROTEIN MATRICES FOR TISSUE ENGINEERING

This application is a CIP of 09/146,153 filed Aug. 27, 1998, now abandoned.

FIELD OF THE INVENTION

The invention relates to the use of matrices that contain pharmaceutically active molecules, including fusion proteins of pharmaceutically active molecules, particularly growth factors, using affinity binding interactions, for use in tissue repair or regeneration and/or controlled release of the pharmaceutically active molecules.

This application claims priority to U.S. patent application No. 09/141,153, filed Aug. 27, 1998, (now abandoned).

BACKGROUND OF THE INVENTION

For tissue repair or regeneration, cells must migrate into a wound bed, proliferate, express matrix components or form extracellular matrix, and form a final tissue shape. Multiple cell populations must often participate in this morphogenetic response, frequently including vascular and nerve cells. Matrices have been demonstrated to greatly enhance, and in some cases have been found to be essential, for this to occur. Natural cell in-growth matrices are subject to remodeling by cellular influences, all based on proteolysis, e.g. by plasmin (degrading fibrin) and matrix metalloproteinases (degrading collagen, elastin, etc.). Such degradation is highly localized and occurs only upon direct contact with the migrating cell. In addition, the delivery of specific cell signaling proteins such as growth factors is tightly regulated. In the natural model, macroporous cell in-growth matrices are not used, but rather microporous matrices that the cells can degrade, locally and upon demand, as the cells migrate into the matrix.

Controlled delivery devices for growth factors have been designed previously based on use of immobilized heparin to sequester the growth factor of some form. For example, Edelman et al. have used heparin-conjugated SEPHAROSE™ beads within alginate. The beads serve as reservoirs that release basic fibroblast growth factor ("bFGF") slowly based on the binding and dissociation of bFGF with heparin.

It has been demonstrated that bi-domain peptides, which contain a factor XIIIa substrate sequence and a bioactive peptide sequence, can be cross-linked into fibrin gels and that this bioactive peptide retains its cellular activity in vitro (Schense, J. C., et al. (1999) *Bioconj. Chem.* 19:75–81). While peptides can partially mimic the bioactivity of the whole protein from which they are derived, this bioactivity is usually lower than the bioactivity of the whole protein, and sometimes it is impossible to mimic certain proteins with only a short peptide. It would therefore be desirable to be able to incorporate the entire protein, such as a growth factor or other pharmaceutically active molecule, into the matrix.

While delivery systems for proteins and growth factors exist and are known, there remains a need for a matrix for use in tissue repair that promotes cellular migration and tissue in-growth into the matrix through the control of growth factor presentation and release to the migrating cells and control of cellular adhesion sites. The need is particularly great for such in-growth matrices that could locally present growth factors and retain their influence and activity locally, through affinity interactions with the matrix, as occurs in nature.

It is therefore an object of the present invention to provide natural, biodegradable matrices for tissue repair, regeneration, and remodeling having incorporated therein growth factors which retain the activity of the intact growth factor molecules.

It is a further object of the present invention to provide natural, biodegradable matrices for controlled and/or sustained release of growth factors.

SUMMARY OF THE INVENTION

Proteins are incorporated into protein or polysaccharide polymer matrices or gels for use in tissue repair, regeneration and/or remodeling and/or drug delivery. The proteins can be incorporated so that they are released by degradation of the matrix, by enzymatic action and/or diffusion. As demonstrated by the examples, one method is to bind heparin to the matrix by either covalent or non-covalent methods, to form a heparin-matrix. The heparin then non-covalently binds heparin-binding growth factors to the protein matrix. If the protein to be bound does not contain a native heparin-binding sequence, a fusion protein can be constructed containing the native protein sequence and a synthetic heparin-binding domain. Alternatively, a fusion protein can be constructed which contains a crosslinkable region(s) and the native protein sequence, and this fusion protein can be sequestered by cross-linking it to form a matrix. The fusion protein or peptide domain can contain a degradable linkage that contains hydrolytic or enzymatic cleavage sites. This allows the rate of delivery to be varied at different locations within the matrix depending on cellular activity at that location and/or within matrix. This approach can be particularly useful when long-term drug delivery is desired, for example in the case of nerve regeneration, where it is desirable to vary the rate of drug release spatially as a function of regeneration, e.g., rapidly near the living tissue interface and more slowly farther into the injury zone. Additional benefits include the lower total drug dose within the delivery system, and spatial regulation of release which permits a greater percentage of the drug to be released at the time of greatest cellular activity. The examples demonstrate optimized ratios or levels of growth factor, heparin binding domain, and heparin or heparin binding peptide sequestered within the matrix that optimally induced cell in-growth and tissue regeneration.

DETAILED DESCRIPTION OF THE INVENTION

Figure 1:
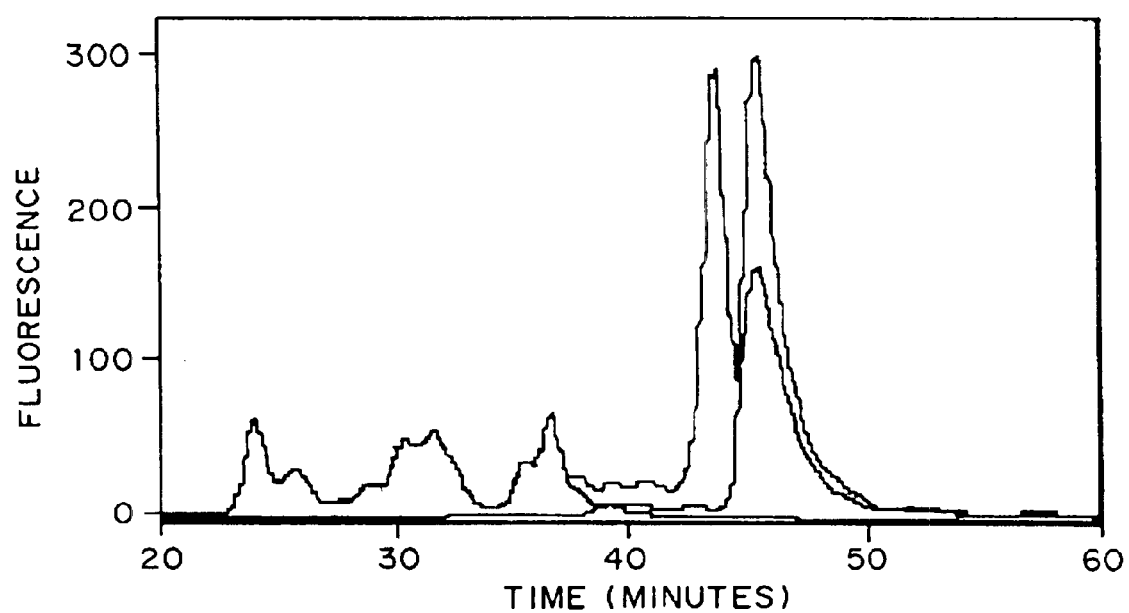
FIG. 1 is a fluorescence detection chromatograms of plasmin-degraded peptide-containing fibrin gels and free peptide. Size exclusion chromatography of a degraded fibrin gel with the $_2Pl_{1-7}$-ATIII$_{121-134}$peptide incorporated (–), with the same peptide free added to the degraded fibrin gel containing incorporated peptide (***), and free peptide alone (- -), are shown. The N-terminal leucine residue was dansylated (abbreviated dL). The free peptide eluted at longer times, corresponding to a lower molecular weight, than did the peptide incorporated into the fibrin gel during coagulation, demonstrating covalent attachment to degraded fibrin and thus covalent incorporation via the action of factor XIIIa activity.

As described herein, a method to enhance tissue repair, regeneration or remodeling or for drug delivery, using protein or polysaccharide polymeric matrices having growth factors releasably incorporated therein, has been developed. There are several advantages over the prior art matrices: the natural matrices are biocompatible and biodegradable and can be formed in vitro or in vivo, at the time of implantation; full length growth factor proteins can be incorporated and retain full bioactivity; the growth factors can be releasably incorporated, using techniques that provide control over how and when and to what degree the growth factors are released, so that the matrix can be used for tissue repair directly or indirectly, using the matrix as a controlled release vehicle.

I. Matrices and Growth Factors

A. Matrix Materials

The matrix is formed by crosslinking ionically, covalently or by combinations thereof, one or more polymeric materials to form a polymeric matrix having sufficient inter-polymer spacing to allow for ingrowth or migration into the matrix of cells.

In the preferred embodiment, the matrix is formed of proteins, most preferably proteins naturally present in the patient into which the matrix is to be implanted. The most preferred protein is fibrin, although other proteins such as collagen and gelatin can also be used. Polysaccharides and glycoproteins may also be used. In some embodiments, it is also possible to use synthetic polymers which are crosslinkable by ionic or covalent binding.

The matrix material is preferably biodegradable by naturally present enzymes. The rate of degradation can be manipulated by the degree of crosslinking and the inclusion of protease inhibitors in the matrix.

B. Degradable Linkages

The proteins forming the matrix can be modified through inclusion of degradable linkages. Typically, these will be enzyme cleavage sites, such as the site for cleavage by thrombin. Moreover, the fusion proteins or peptide chimeras, which are cross-linked to fibrin gels, may be further modified to contain a degradable site between the attachment site (i.e. factor XIIIa substrate or heparin-binding domain) and the bioactive protein (i.e., growth factor or enzyme). These sites may be degradable either by non-specific hydrolysis (i.e. an ester bond) or they may be substrates for specific enzymatic (either proteolytic or polysaccharide degrading) degradation. These degradable sites allow the engineering of more specific release of bioactive factor from fibrin gels. For example, degradation based on enzymatic activity allows for the release of bioactive factors to be controlled by a cellular process rather than by diffusion of the factor through the gel.

The degradation sites allow the bioactive factor to be released with little or no modification to the primary protein sequence, which may result in higher activity of the factor. In addition, it allows the release of the factor to be controlled by cell specific processes, such as localized proteolysis, rather than diffusion from some porous materials. This allows a factors to be released at different rates within the same material depending on the location of cells within the material. Cell specific proteolytic activity is vital in applications such as nerve regeneration, which occur over long periods of time. This also reduces the amount of total growth factor needed, since its release is controlled by cellular processes. Conservation of growth factor and its bioavailability are distinct advantages of exploiting cell specific proteolytic activity over the use of diffusion controlled release devices which characteristically result in the loss of a significant amount of bioactive factor in an initial burst release.

Enzymes that could be used for proteolytic degradation are numerous. Proteolytically degradable sites could include substrates for collagenase, plasmin, elastase, stromelysin, or plasminogen activators. Exemplary substrates are listed below. P1–P5 denote amino acids 1–5 positions toward the amino terminus of the protein from the site were proteolysis occurs. P1'–P4' denote amino acids 1–4 positions toward the carboxy terminus of the protein from the site where proteolysis occurs.

TABLE 1

Sample substrate sequences for protease SEQ ID Nos:2–9.

| Protease | P5 | P4 | P3 | P2 | P1 | P1' | P2' | P3' | P4' | Reference |
|---|---|---|---|---|---|---|---|---|---|---|
| Plasmin | | | L | I | K | M | K | P | | Takagi and Doolittle, (1975) Biochem. 14:5149–5156 |
| Plasmin | | | N | F | K | S | Q | L | | Takagi and Doolittle, 1975 |
| Stromelysin | Ac | G | P | L | A | L | T | A | L | Smith et al., (1995). J. Biol. Chem. 270:6440–6449 |
| Stromelysin | | Ac | P | F | E | L | R | A | NH$_2$ | Smith et al., 1995 |
| Elastase | | | Z- | A | A | F | A | NH$_2$ | | Besson et al., (1996) Analytical Biochemistry 237:216–223. |

TABLE 1-continued

Sample substrate sequences for protease SEQ ID Nos:2–9.

| Protease | P5 | P4 | P3 | P2 | P1 | P1' | P2' | P3' | P4' | Reference |
|---|---|---|---|---|---|---|---|---|---|---|
| Collagenase | | G | P | L | G | I | A | G | P | Netzel-Arnett et al., (1991) J. Biol. Chem.. 266:6747–6755 |
| t-PA | P | H | Y | G | R | S | G | G | | Coombs et al., et al, 1998. J. Biol. Chem. 273:4323–4328 |
| u-PA | P | G | S | G | R | S | A | S | G | Coombs et al., 1998 |

Polysaccharide substrates: Enzymatic degradation can occur with polysaccharide substrates for enzymes such as heparinase, heparitinase, and chondroitinase ABC. Each of these enzymes have polysaccharide substrates. By virtue of the presence of heparin in all of the heparin-binding systems, the substrate for heparinase is already built into these systems.

Proteolytic substrates: Proteolytic substrate could be added during the peptide synthesis of either the peptide chimera or the heparin-peptide chimera. The heparin-binding peptide chimera could be modified to contain a proteolytic degradation sequence by inserting a protease substrate, such as one of the one for plasmin described above, between the factor XIIIa substrate and the heparin-binding domain. The heparin-peptide chimera could be modified to contain a proteolytic degradation sequence by inserting a protease substrate, such as one of the one for plasmin described above, between the factor XIIIa substrate and the heparin domain. A substrate with a high $K_m$ and a low $k_{cat}$ could be used to slow cleavage while occupying active sites of the protease. The cleavage substrates other than those for plasma could be used to allow release of the bioactive factors to be independent of matrix degradation.

Oligo-esters: An oligo-ester domain could be inserted between the factor XIIIa substrate and either the heparin-binding domain or the heparin domain of the chimera during the peptide synthesis step as well. This could be accomplished using an oligo-ester such as oligomers of lactic acid.

Non-enzymatic degradation substrate can consist of any linkage which undergoes hydrolysis by an acid or base catalyzed mechanism. These substrates can include oligo-esters such as oligomers of lactic or glycolic acid. The rate of degradation of these materials can be controlled through the choice of oligomer.

C. Heparin; Heparin Binding Peptides

The matrix can be modified through the inclusion of heparin and/or heparin binding fragments, which bind directly or indirectly to proteins which bind to heparin. In the latter case, the peptide can bind to heparin, which is then available for binding to factors which include a heparin binding site, or the peptide can itself contain a heparin portion which is bound by certain heparin-binding growth factors. These can be attached to the matrix material using standard techniques, as discussed in more detail below.

In a preferred embodiment, heparin is attached to fibrin gels non-covalently using a two-part system consisting of a peptide chimera and heparin itself. The peptide chimera consists of two domains, a factor XIIIa substrate and a polysaccharide-binding domain. Once the peptide chimera is cross-linked into the fibrin gel, it attaches the heparin (or other polysaccharides) by non-covalent interactions.

Numerous proteins have been found to have heparin-binding affinity. Some of these proteins and the sequences of their heparin-binding domains are listed below in Table 2. These are also discussed under the section relating to bioactive factors which can be delivered by the polymeric matrix.

TABLE 2

Heparin-binding sequences SEQ ID NOS: 10–19

| Protein | Heparin-binding domain | Reference |
|---|---|---|
| Anti-thrombin III | K(A)FAKLAARLYRKA | (Tyler-Cross, R., et al, (1994). Protein Science. 3:620–627) |
| Platelet Factor 4 | YKKIIKKL | Zucker and Katz, (1991). Exper. Biol. Med.:693–702 |
| Neural Cell Adhesion Molecule | KHKGRDVILKKDVR | Kallapur, et al, (1992) J. Neurosci. Res. 33:538–548 |
| Fibronectin | YEKPGSPPREVVPRPRPCV KNNQKSEPLIGRKKT | Haugen, et al, (1992). J. Neurosci. 12:2034–2042 |
| bFGF (basic fibroblast growth factor) | KDPKRL YRSRKY | SwissPROT: P09038 |
| aFGF (acidic fibroblast growth factor) | YKKPKL | SwissPROT: P05230 |
| LPL (lipoprotein lipase) | AKRSSKM CRKRCN | Hata, et al., J. Biol. Chem. 268:8447–8457 |

D. Bioactive Factors

Many growth factors that are involved in morphogenesis, both in the developing organism and in the adult, bind to extracellular matrix molecules. This affinity provides for a local mode of action of the morphogen, preventing uncontrolled distal influences. The principal matrix affinity interaction that is involved in this localization of influence is for heparin and heparin-sulfate proteoglycans. Growth factors that bind to heparin include the transforming growth factor ("TGF")-beta superfamily (including the bone morphogenic proteins, "BMPs"), the fibroblast growth factor ("FGF") family, and vascular epithelial growth factor ("VEG"), among others. In general, a growth factors which are considered to bind heparin will elute from a heparin-affinity column at NaCl concentrations above physiological levels (greater than or equal to 140 mM). Additional "heparin-binding" growth factors include interleukin-8, neurotrophin-6, heparin-binding epidermal growth factor, hepatocyte growth factor, connective tissue growth factor, midkine, and heparin-binding growth associated molecule. These growth factors have been shown to regulate tissue repair.

Heparin-binding domains naturally occur in many different families of growth factors. One of these families with one or more member that bind heparin are the fibroblast growth factors (Presta, M., et al. (1992). *Biochemical and Biophysical Research Communications.* 185:1098–1107). Additional growth factors which bind heparin include transforming growth factor, bone morphogenetic factor, interleukin-8, neurotrophin-6, vascular endothelial cell growth factor, heparin-binding epidermal growth factor, hepatocyte growth factor, connective tissue growth factor, midkine, and heparin-binding growth associated molecule (Götz, R., et al., (1994), *Nature.* 372:266–269; Kaneda, N.

et al., (1996) *J. Biochem.* 119:1150–1156; Kiguchi, K., et al., (1998) *Mol. Carcinogensis.* 22:73–83; Kinosaki, M., et al., (1998). *Biochim. Biophys. Acta.* 1384:93–102; McCaffrey, T., et al., (1992) *J. Cell. Physiol.* 152:430–440; Nolo, R., et al., (1996) *Eur. J. Neurosci* 8:1658–1665; Spillmann, D., et al., (1998). *Journal of Biological Chemistry.* 273:15487–15493; Steffen, C., et al. (1998); *Growth Factors.* 15:199–213.

Tessler, S., et al., (1994) *J. Biol. Chem.* 269:12456–12461). These factors have shown the potential to enhance healing in many different types of tissue including vasculature, skin, nerve and liver. Therefore, these materials can be used to enhance wound healing in many different parts of the body by selecting the appropriate growth factor.

II. Methods for Incorporation and/or Release of Bioactive Factors.

In the preferred embodiment for incorporation of a growth factor or other bioactive protein within the matrix, the matrix is formed of fibrin and the exogenous molecules incluse a substrate which will be incorporated within fibrin during coagulation. Exogenous peptides can be designed to include two domains, one domain which is a substrate for a crosslinking enzymes such as XIIIa. Factor XIIIa is a transglutaminase that is active during coagulation. This enzyme, formed naturally from factor XIII by cleavage by thrombin, functions to attach fibrin chains to each other via amide linkages, formed between glutamine side chains and lysine side chains. The enzyme also functions to attach other proteins to fibrin during coagulation, e.g. the protein alpha 2 plasmin inhibitor. The N-terminal domain of this protein, specifically the sequence NQEQVSP (SEQ ID NO:20), has been demonstrated to function as an effective substrate for factor XIIIa. A second domain on this peptide can then be selected to be a bioactive factor, such as a peptide, or a protein, or a polysaccharide (Sakiyama-Elbert, et al., (2000) *J. Controlled Release* 65:389–402) and herein. As such, exogenous bioactive factors may be incorporated within fibrin during coagulation via a factor XIIIa substrate.

A. Use of Heparin Affinity in Release of Proteins

A simple way to incorporate many bioactive proteins of interest in healing and regeneration into fibrin is to attach heparin by one of the methods described herein to the fibrin gels and use the heparin to sequester heparin-binding proteins, such as heparin-binding growth factors. This can be accomplished one of two ways, either indirectly by cross-linking a heparin-binding peptide into the fibrin gel and binding heparin to this peptide non-covalently (using a bi-functional peptide containing a heparin-binding domain and a factor XIIIa substrate), or by directly coupling a heparin-peptide chimera (where the heparin is chemically attached to a peptide containing a factor XIIIa substrate). Regardless of the method of incorporation, the incorporated heparin can then sequester proteins, such as growth factors with heparin binding affinity, in the fibrin gel in a manner similar to the way that they are sequestered to the extracellular matrix in nature. Heparin can also protect these factors from proteolytic degradation and prolong their activity until they are released from the matrix.

Incorporation of Heparin through the Incorporation of a Heparin-binding Peptide

The attachment of heparin, either covalent or non-covalently to fibrin gels, adds a novel functionality to these materials. The attachment of heparin permits the fibrin matrix to bind heparin-binding proteins, including growth factors in a manner which does not harm the protein, and prevents free diffusion of the protein from the gel. This allows for the controlled-release of heparin-binding proteins by one of two mechanisms, either degradation of the gel by binding of the protein to some other high affinity protein, such as a cell surface receptor.

Heparin can be attached to fibrin gels non-covalently using a two-part system consisting of a peptide chimera and heparin itself. The peptide chimera consist of two domains, a factor XIIIa substrate and a polysaccharide-binding domain. Once the peptide chimera is cross-linked into the fibrin gel, it attaches the heparin (or other polysaccharides) by non-covalent interactions.

In order to sequester growth factors which do not spontaneously bind heparin, it is necessary to modify the protein through the addition of a functionality capable of attaching to fibrin. This can be accomplished in several ways. By way of example, this may be achieved through the addition of a factor XIIIa substrate or by adding a heparin-binding domain to the resulting fusion protein.

The addition of a synthetic factor XIIIa substrate can be accomplished by expressing a fusion protein containing the native growth factor sequence and a factor XIIIa substrate at either the amino or carboxyl terminus of the fusion protein. This modification is done at the DNA level. Whole proteins present difficulty in that they are synthesized by solid phase chemical synthesis. The DNA sequence encoding the growth factor is adapted to optimal codon usage for bacterial expression. The DNA sequence is then determined for the desired Factor XIIIa substrate, using codons which occur frequently in bacterial DNA.

A series of gene fragments is designed prior to the DNA synthesis. Due to the error frequency of most DNA synthesis, which contains an error approximately every 50 bp, genes are constructed to be approximately 100 bp in length. This reduces the number of colonies that must be screened in order to find one containing the proper DNA sequence. The location at which one gene ends and the next begins is selected based on the natural occurrence of unique restriction enzyme cut sites within the gene, resulting in fragments (or oligonucleotides) of variable length. The process is greatly assisted by the use of software which identifies the location and frequency of restriction enzyme sites within a given DNA sequence.

Once the gene fragments have been successfully designed, common restriction enzyme sites are included on the ends of each fragment of allow ligation of each fragment into a cloning plasmid. For example, adding EcoRI and HindIII sites to each gene fragment allows it to be inserted into the polylinker cloning region of pUC 19. The 3' and 5' single strands of each gene fragment are then synthesized using standard solid phase synthesis with the proper sticky ends for insertion into the cloning vector. Following cleavage and desalting, the single stranded fragments are then purified by PAGE and annealed. After phosphorylation, the annealed fragments are ligated into a cloning vector, such as pUC 19.

Following ligation, the plasmids are transformed into DH5-F' competent cells and plated on Isopropyl-D-Thiogalactopranoside(IPTG)/5-Bromo-4-chloro-3-indolyl-D-Galactopyranoside (X-gal) plates to screen for insertion of the gene fragments. The resulting colonies which contain gene fragments are then screened for insertion of the proper length. This is accomplished by purifying plasmid from colonies of transformed cells by alkaline lysis miniprep protocol and digesting the plasmid with the restriction enzymes sites present at either end of the gene fragment. Upon detection of the fragments of the proper length by agarose gel electrophoresis, the plasmids are sequenced.

When a plasmid containing a gene fragment with the proper sequence is identified, the fragment is then cut out and used to assemble the full gene. Each time one plasmid is cut with the enzymes at the insertion points and purified from an agarose gel after dephosphorylation of the plasmid. Meanwhile, a second plasmid containing the fragment to be inserted is also cut and the fragment to be inserted is purified from an agarose gel. The insert DNA is then ligated into the dephosphorylated plasmid. This process is continued until the full gene is assembled. The gene is then moved into an expression vector, such as pET 14b and transformed into bacteria for expression. After this final ligation, the full gene is sequenced to confirm that it is correct.

Expression of the fusion protein is accomplished by growing the bacteria until they reach mid-log phase growth and then inducing expression of the fusion protein. Expression is continued for approximately 3 hours and the cells are then harvested. After obtaining a bacterial cell pellet, the cells are lysed. The cell membranes and debris are removed by washing the cell lysate pellet with Triton X100, leaving the inclusion bodies in relatively pure form. The fusion protein is solubilized using high urea concentrations and purified by histidine affinity chromatography. The resulting protein is then renatured gradually by dialysis against a slowly decreasing amount of urea and lyophilized.

Incorporation of Heparin through the Incorporation of a Heparin-Peptide Chimera

Polysaccharide grafts (heparin—factor XIIIa substrate peptide chimera) can be incorporated within fibrin during coagulation to provide immobilized heparin sites to bind growth factors and slow their release. Heparin (or other polysaccharides such as heparin sulfate or chondroitin sulfate) can be attached to fibrin directly using factor XIIIa by constructing a heparin-peptide chimera. This chimera contains two domains, a peptide domain consisting of a factor XIIIa substrate and the polysaccharide domain such as heparin. These chimeras are made using modified heparin (or another polysaccharide), e.g., which contains a unique reactive group at one end to control the site where peptide coupling occurs on the heparin molecule. Through the use of a unique functional group on the peptide, such as a side chain present only on the end of the peptide where coupling is desired, the location of coupling on the peptide can be controlled as well. It is also possible to incorporate the factor XIIIa substrate peptide along the chain of heparin, as opposed to at the terminus, and even to incorporate more than one such peptide per heparin chain, but the preferred approach is to incorporate a single factor XIIIa substrate peptide at one end of the heparin. These chimeras can then be covalently cross-linked to fibrin gels during coagulation by the enzymatic activity of factor XIIIa, allowing direct attachment of heparin to the fibrin gel.

Role of Concentration of Heparin in Determining the Release Rate of Proteins

Determination of the optimal ratios of growth factor:heparin-peptide chimera or the optimal ratio of growth factor;Heparin:heparin binding peptide as well as the optimal density of the heparin-peptide chimera or the heparin binding peptide incorporated into the fibrin is important. Despite their relatively strong affinity for heparin, heparin-binding growth factors dissociate from the matrix on a short time scale. Therefore, a high excess of binding sites ensures that the growth factor does not diffuse far before binding to the matrix again. This equilibrium also allows for the binding of free growth factor to cell surface receptors that are in close proximity to the site of dissociation. This method of controlled release provides both relatively long term binding of growth factors and rapid release of growth factors to local cells. As described herein, however, it is not always the case that a high ratio, and thus a slow rate of release, provides the most desirable biological response. There may be cases where more rapid rates of release are desirable, especially with some growth factors.

It has been attempted to mathematically predict what ratio of binding site to growth factor is optimal for cell growth applications as determined by very slow growth factor release. It was demonstrated that the rate of passive release of growth factor from the matrix could be modulated through the ratio of peptide and heparin to the heparin-binding growth factor, higher excesses of heparin and heparin-binding peptide relative to the heparin-binding growth factor leading to slower passive release. It is not always possible to use such methods to predict the optimal release characteristics, however. For example, the examples demonstrate that BMP-2 may be advantageously released more rapidly from a material with a ratio of heparin and heparin-binding peptide to BMP-2 that is closer to equimolar. In some case better results are obtained with lower heparin to growth factor ratios.

The ability of the heparin-containing delivery system to deliver growth factors in an active form was tested in an ectopic model of bone formation, where fibrin matrices containing the delivery system and BMP-2 were implanted subcutaneously in rats. In this model, favorable conditions for bone formation were at low heparin to growth factor ratios of 1:1. The addition of higher ratios such as 5:1 or greater, were inhibitory to bone formation. These results were unexpected based on previous published studies and suggest that low heparin to growth factor ratios have unanticipated use in delivery of BMP-2. (See Example 5).

Addition of exogenous factor XIII to fibrinogen preparations can be used to increase the number of heparin-binding peptides incorporated with fibrin matrices, allowing the heparin-binding peptide to serve both as an immobilization site for heparin and a cell adhesion site. This increase in peptide concentration might enhance the ability of such materials to promote neurite extension, and other forms of cell migration, through the use of heparin-binding domains as cell adhesion sites. It has been demonstrated that heparin-binding peptides act as adhesion peptides and as such can enhance the rate of cell migration within fibrin (Sakiyama, S. E. et al., (199) $FASEB$ $J.$ 13:2214–2224). However, this response required ca. 8 moles of incorporated peptide per mole of fibrinogen in the clot. As such, use of a large number of these heparin-binding peptides to bind heparin for use as an affinity site in the sustained release of heparin-binding growth factors can remove the beneficial adhesion effect of the heparin binding peptide. This limitation can be overcome by incorporation of higher levels of the exogenous heparin-binding peptide, which can be accomplished through the addition of higher levels of factor XIIIa to the fibrinogen preparation, thus permitting the peptide to have both effects simultaneously. The incorporation of additional peptide at ratio greater than 8 moles of peptide per mole fibrinogen (i.e. 25 moles of peptide per mole fibrinogen) might thus be useful for allowing the heparin-binding peptides to serve both as cell adhesion sites and heparin immobilization sites for drug delivery. For example, 5% of the heparin-binding sites might be used to immobilize heparin for drug delivery and the other 95% would remain unoccupied and free to serve as cell adhesion domains, thus allowing the heparin-binding peptides to be used as both cell adhesion domains and growth factor immobilization sites within the same material. This dual use of a heparin-binding peptides benefits from the use of exogenous factor XIIIa because it has been shown that a relatively high number of heparin-binding sites must be incorporated into fibrin (8 moles of peptide per mole fibrinogen) in order to enhance cell adhesion and migration within fibrin matrices.

Use of Bi-domain Peptides for Incorporation of Heparin Affinity Sites.

These exist many possible combinations of peptide-peptide chimeras, with a factor XIIIa substrate on one domain and a heparin-binding peptide on the other domain. These different combinations will have different advantages and disadvantages. For example, some factor XIIIa substrates are more efficiently incorporated than others. Additionally, different heparin-binding peptides have different affinity for heparin. One additional consideration is the possible immunogenicity of the peptides. Even though it is possible to utilize peptide sequences based on the sequences of the human proteins, the fusion between these two human sequences is new and would have been seen by the immune system of a patient. As such, there exists some risk that such a fusion would be immunogenic and induce antibody formation against one or the other proteins, or against the fusion site itself. In general, shorter peptide sequences will have a lesser tendency to induce antigenic responses than longer ones. As such, the chimera with the alpha 2 plasmin inhibitor factor XIIIa substrate and the antithrombin III heparin binding domain would be somewhat more likely to induce an antigenic response than the corresponding bi-domain peptide with a heparin binding domain from platelet factor 4, for example.

An additional approach to reduce the probability than a bi-domain chimera used to immobilize heparin within the fibrin network will be immunogenic is to form a peptide-heparin chimera directly, with a factor XIIIa substrate, for example from the protein alpha 2 plasmin inhibitor, in one domain, and a heparin chain as the other domain, with a covalent bond between the two. In this manner, no non-natural peptide sequence exists at the fusion site, so the potential for immunological interactions is very low.

Use of Fusion Proteins in Release of Proteins

One may further consider use of fusion proteins in release of proteins through affinity for heparin, in that a fusion of a bioactive protein that does not bind heparin may be constructed with a heparin-binding domain, to make a resulting fusion protein that does bind heparin. Moreover, as an alternative to the incorporation of bioactive proteins within fibrin via their affinity for heparin, the proteins may be incorporated directly using factor XIIIa. This is possible if they possess a substrate domain for factor XIIIa, either naturally or by incorporation within a recombinant protein to form a fusion protein with the bioactive protein and a factor XIIIa substrate domain.

Synthesis of either of the fusion proteins described above can be accomplished by utilizing molecular biology techniques. To do this, a fusion protein can be created that contains the entire protein sequence of interest with a cross-linking or binding sequence fused onto the amino or carboxyl terminus, or potentially elsewhere within the protein chain. This is done of the DNA level, as sequences coding for either a factor XIIIa cross-linking substrate or a heparin-binding domain can be inserted at the beginning or the end of the codons for the original protein, for example. When these modified proteins are expressed, they will then contain the additional domain of interest at the amino or carboxy terminus, or elsewhere within the main protein domain. By using the natural machinery designed for protein synthesis, it becomes possible to synthesize and purify large proteins with high fidelity.

Using standard molecular biology techniques, fusion proteins can be made of any growth factor for which the protein or DNA sequence is known, allowing the addition of novel domains such as heparin-binding domains or enzymatic substrates. These fusion proteins can be constructed so as to add a novel domain to either the N or C-terminus of the protein, for example or within the protein chain. The modifications are made at the DNA level by constructing a gene containing both the DNA sequence coding for the growth factor and the DNA sequence coding for the crosslinking or binding sequence, for example, a heparin-binding domain. This DNA is then ligated into an expression plasmid and transformed into bacteria. Upon induction of expression, the bacteria will produce large amounts of this fusion protein. Following expression, the protein must be purified from the cell lysate and refolded. Purification is often simplified due to the tendency of mammalian proteins expressed at high level to form inclusion bodies in bacteria.

Design of Fusion Proteins for Incorporation

A recombinant fusion protein can be incorporated into the fibrin gels using several different schemes. In the first design, a factor XIIIa substrate has been directly incorporated onto the protein. When this modified protein is present during the polymerization of the fibrin, it is directly incorporated into the fibrin matrix in a manner similar to the bi-domain peptides. A separate method involves fusion proteins that have been synthesized to incorporate a heparin-binding domain. In this example, a bi-domain peptide, heparin, and the heparin-binding fusion protein are included in the fibrin polymerization mixture. During polymerization, the bi-domain peptide is cross-linked into the fibrin gel. This bi-domain peptide would contain a factor XIIIa substrate sequence in addition to a heparin-binding sequence. The heparin binds to the bi-domain peptide that has been incorporated in the fibrin gel and is trapped in the fibrin matrix. This entrapped heparin serves to sequester the heparin-binding fusion protein within the fibrin gel by binding to the engineered heparin-binding domains. This until the cross-linked peptide is removed from the gel via cell controlled proteolysis.

This technique can be further modified by incorporating an enzymatic degradation site between the factor XIIIa substrate sequence and the protein of interest. By careful selection of $K_m$ and $k_{cat}$ of this enzymatic degradation site, degradation could be controlled to occur either before or after the protein matrix and/or by utilizing similar or dissimilar enzymes to degrade the matrix, with the placement of the degradation site being tailored for each type of protein and application. This new protein could be directly cross-linked into the fibrin matrix as described above. However, incorporating an enzymatic degradation site alters the release of the protein during proteolysis. When the cell-derived proteases reach the sequestered protein, they can cleave the engineered protein at the newly formed degradation site. The resulting degradation products would include the liberated protein, which would now be nearly free of any engineered fusion sequences, as well as any degraded fibrin. Therefore, the free protein would now be nearly identical in primary sequence to the native growth factor and potentially more bioactive. A similar method can be used with the heparin-binding fusion proteins. These new proteins would then contain the protease degradation site, as well as the new heparin-binding domain. The heparin-binding fusion proteins will be sequestered into the matrix by the incorporation of heparin into the fibrin via the covalent immobilization of heparin-binding peptides. Once again, with the new protease degradation site added, the released protein would be identical in primary sequence to the natural protein.

III. Methods of Use

The polymers described herein can be crosslinked to form matrices for repair, regeneration, or remodeling of tissues, and/or release of bioactive factors, prior to or at the time of implantation. In some cases it will be desirable to induce crosslinking at the site of administration to conform the matrix to the tissue at the implantation site. In other cases, will be convenient to prepare the matrix prior to implantation, and in the case where the matrix incorporates heparin or heparin-binding peptides which are used to bind other bioactive molecules such as growth factors, these factors may be added to the matrix prior to or at the time of implantation. It may be convenient in some cases as well to "re-fill" the matrix with these bioactive factors, where the originally loaded factors have been released.

Crosslinking can be achieved through the addition of exogenous crosslinking agent, or in the case where the polymer includes a factor XIIIa substrate, during surgical procedures or by addition of thrombin locally at the site of implantation.

Cells can also be added to the matrix prior to or at the time or implantation, or even subsequent to implantation, either at or subsequent to crosslinking of the polymer to form the matrix. This may be in addition to or in place of crosslinking the matrix to produce interstitial spacing designed to promote cell proliferation or in-growth.

Although in most cases it will be desirable to implant the matrix to promote cell growth or proliferation, in some cases the bioactive factors will be used to inhibit the rate of cell proliferation. A specific application is to inhibit the formation of adhesions following surgery.

The following examples are included to demonstrate preferred embodiments of the invention. While the compositions and methods have been described in terms of preferred embodiments, it will be apparent to those of skill in the art that variations may be applied to the composition, methods and in the steps or in the sequence of steps of the method described herein without departing from the concept, spirit and scope of the invention.

EXAMPLE 1

Indirect Couple of Heparin via a Heparin-binding Peptide to attach growth factor.

A peptide chimera containing both a factor XIIIa substrate and a heparin-binding domain was synthesized by standard solid phase synthesis. A sample peptide is one containing the following sequence, dLNQEQVSPK(A)FAKLAARLYRKA (SEQ IN NO:21), where the N-terminus of the peptide contains the factor XIIIa substrate and the sequence in italics contains a modified peptide from the heparin-binding domain of ATIII (dL denotes dansyl leucine, which is used to allow detection of the peptide by fluorescence).

Size exclusion chromatography was used to determine the amount of peptide cross-linked to fibrin gels using the previously developed incorporation method. A bi-domain peptide containing the heparin-binding domain from anti-thrombin III and a flourescent label was incorporated into fibrin gels during polymerization. The free peptide was washed from the gels, and the fibrin network was degraded with plasmin. The degradation products were analyzed by high performance liquid chromatography (size exclusion chromatography) to determine the amount of peptide (by fluorescence) present per mole of fibrinogen (by UV absorbance). The fluorescence signal from peptide-modified gels appeared at an earlier elution time than did the signal from free peptide alone, indicating that all peptide present in the modified gels was cross-linked to fibrin (FIG. 1). Quantification based on standards of known concentration for both peptide and fibrin networks degraded with plasmin showed incorporation of 8.7±0.2 moles of peptide per mole of fibrinogen (n=10.

In order to evaluate this approach to release of heparin-binding growth factors from fibrin cell in-growth matrices that also comprises a covalently linked bi-domain peptide, one domain of which is a factor XIIIa substrate and one domain of which is a heparin-binding domain based on antithrombin III, dorsal root ganglia were cultured three-dimensionally within fibrin gels under a variety of conditions, as shown in the below.

Cross-linking Protocol for use of Heparin-Binding Peptides:

1) Dialyze fibrinogen (8 mg/ml) versus 4 L of Tris buffered saline (33 mM Tris), pH 7.4 for 24 hours.
2) Sterile filter fibrinogen using a 0.2 μm syringe filter.
3) Make the following peptide solutions:

|  | Peptide (25 mg/ml) | Heparin (45 mg/ml) | BFGF (5 μg/ml) | Tris buffered saline (TBS) |
|---|---|---|---|---|
| Fibrin | 0 μl | 0 μl | 0 μl | 980 μl |
| Peptide | 70 μl | 0 μl | 0 μl | 910 μl |
| Peptide + heparin | 70 μl | 70 μl | 0 μl | 840 μl |
| Peptide + heparin + bFGF | 70 μl | 70 μl | 56 μl | 784 μl |

4) Make thrombin solution: 100 units in 5 ml TBS.
5) Add 1.4 ml of fibrinogen to each peptide solution.
6) Make gels: Add 20 μl of TBS+50 mM $CaCl_2$, 40 μl of thrombin solution (20 units/ml), and 340 μl of peptide solution+fibrinogen. (above solutions make 6 gels).
7) Incubate at 37° C. for 1 hr.
8) Wash 5 times in 24 hours. Use 1 ml of TBS the first 4 times and neuronal media the last time.
9) Dissect day 8 chick embryonic dorsal root ganglia.
10) Place one ganglia in each gel and place at 37° C. for 1 hr.
11) Add 1 ml of neuronal media to each gel.
12) Change media after 24 hours.

Figure 2:
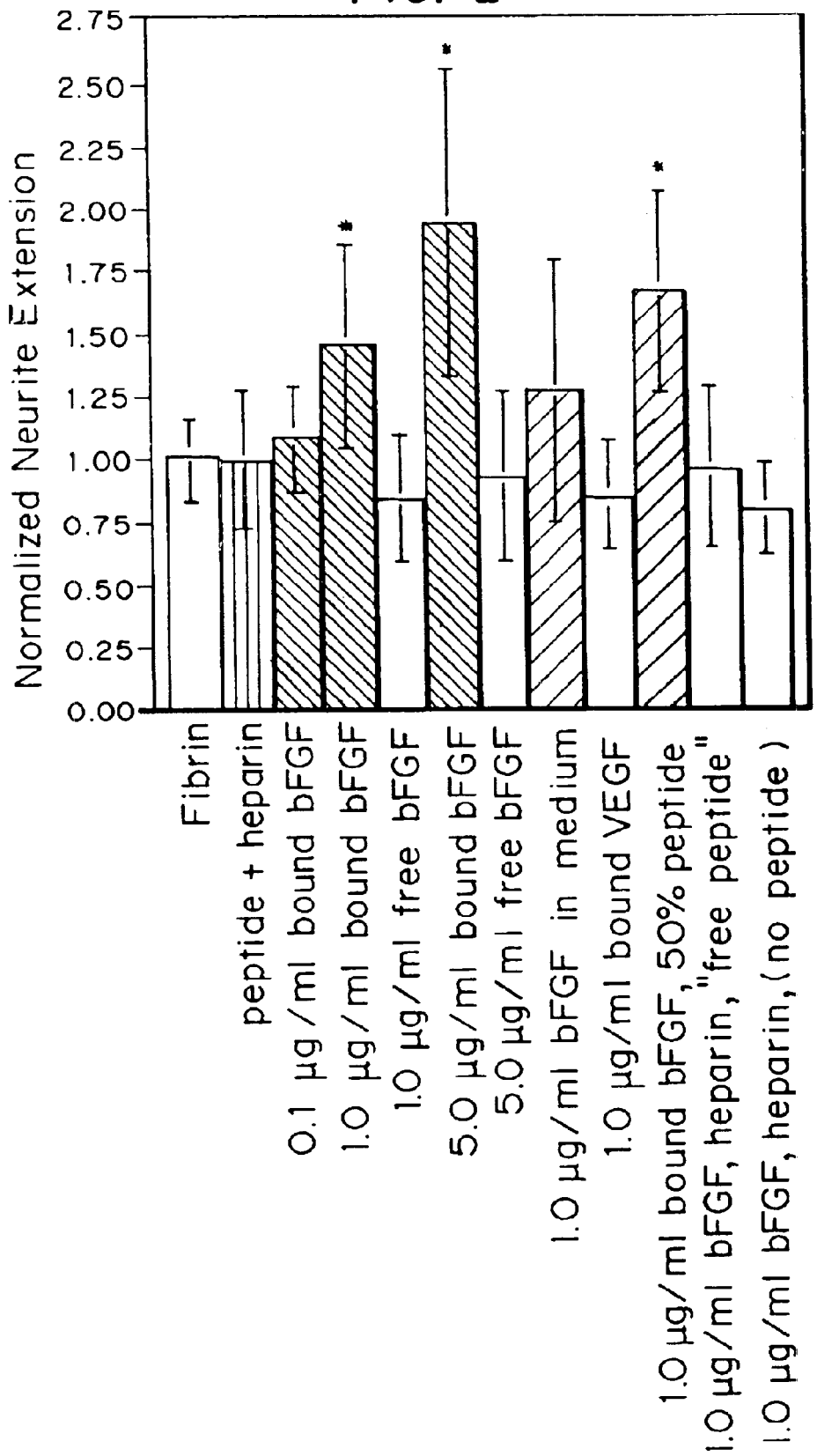
FIG. 2 is a graph of the effect of matrix bound bFGF on dorsal root ganglion (DRG) neurite extension at 48 hr. Mean values and standard deviation of the mean are shown (* dentoes p<0.05 compared with unmodified fibrin.)

The results of these studies with dorsal root ganglion culture are shown in FIG. 2. These results show that the heparin and peptide alone do not increase neurite extension. When added without peptide and heparin, bFGF does not enhance neurite outgrowth, demonstrating that the washing protocol used in sufficient. Neurite enhancement is increased by the addition of both 1 μg/ml and 5 μg/ml of bound bFGF in a dose dependent manner. The addition of 1.0 μg/ml bound VEGF did not increase neurite extension, suggesting that the effect bFGF is not due to its ability to promote angiogenesis.

EXAMPLE 2

Synthesis of Heparin-Peptide Chimeras

A heparin-peptide chimera is synthesized by coupling a peptide, containing the factor XIIIa substrate on the N-terminus and a poly-lysine on the C-terminus, to a heparin oligosaccharide, with a unique aldehyde group on one end, via reductive amination. A peptide with the following sequence, dLNQEQVSPLKKKG (SEQ ID NO:22), is synthesized by standard solid phase peptide chemistry. The heparin oligosaccharides are made by standard nitrous acid degradation of heparin, resulting in the formation of an aldehyde on the reducing terminal of the cleaved oligosaccharide. During coupling, the -amino group of the lysine side chain attacks the aldehyde on the reducing end of the heparin oligosaccharide to form a Schiff base. The Schiff base is then reduced to form a stable product. A sample coupling protocol is given below. One can also couple the heparin to the simple alpha 2 plasmin inhibitor substrate site NQEQVSP (SEQ ID NO:20). A primary amine exists on this peptide only at the N-terminus. When the peptide is synthesized, s usual, on a solid phase resin, the N-terminus is exposed dangling, and when the alpha amine on the terminal N is deprotected, a primary amine is available for reaction. A reactive form of heparin may be readily formed by cleavage in certain acids, as described in Grainger, D., et al., (1988). *J. Biomed. Mat. Res.* 22:231–249, to form a heparin fragment with a terminal aldehyde group. This reactive aldehyde can be passed over the peptide still attached to the resin, condensed there upon, to form a peptide-heparin chimera that is linked by a Schiff base, which may be readily reduced with sodium cyanoborohydride to form a secondary amine, which is a more stable form.

Other approaches could be used. For example, the aldehyde heparin may be converted to a primary amino heparin by reaction with excess ethylene diamine and reduction of the Schiff base, analogous to that described above. Purification from the free residual ethylene diamine can be achieved by dialysis. This amino heparin may be condensed on the C-terminal carboxyl group by cleaving the peptide from the solid resin with the carboxyl group on the E residue still protected, followed by activation of the carboxyl group on the C terminus using standard reagents from peptide synthesis, and then followed by deprotection of the carboxyl group on the E residue.

Coupling Protocol:
1) Dissolve 1.8 mM of peptide and 1.8 mM of nitrous acid degraded heparin in 50 mM borate buffer, pH 9, React for 30 minutes.
2) Add 160 mM NaCNBH$_3$ and react for 12 hours.
3) Add 240 nM NaCNBH$_3$ and react for 12 hours.
4) Adjust pH to 7 with dilute HCl.
5) Add NaCl to a final concentration of 1M.
6) Dialyze versus 4L of deionized water for 24 hours.
7) Lyophilize to obtain reaction product.
8) Analyze reaction yield by size exclusion chromatography.
9) Purification of desired product is accomplished using anion exchange chromatography.

Use: Cross-linking Protocol for use of Heparin-Peptide Chimeras:
1) Dialyze fibrinogen (8 mg/ml) versus 4 L of Tris buffered saline (33 mM Tris), pH 7.4 for 24 hours.
2) Sterile filter fibrinogen using a 0.2 μm syringe filter.
3) Make the following chimera solutions:

|  | heparin-peptide chimera (67 mg/ml) | bFGF (5 μg/ml) | Tris buffered saline (TBS) |
|---|---|---|---|
| Fibrin | 0 μl | 0 μl | 980 μl |
| heparin-peptide chimera | 70 μl | 0 μl | 840 μl |
| heparin-peptide chimera + bFGF | 70 μl | 56 μl | 784 μl |

4) Make thrombin solution : 100 units in 5 ml TBS.
5) Add 1.4 ml of fibrinogen to each chimera solution.
6) Make gels: Add 20 μl of TBS+50 mM CaCl$_2$, 40 μl of thrombin solution (20 units/ml), and 340 μl of chimera solution+fibrinogen. (above solutions make 6 gels).
7) Incubate at 37° C. for 1 hr.
8) Wash 5 times in 24 hours. Use 1 ml of TBS the first 4 times and neuronal media the last time.
9) Dissect day 8 chick embryonic dorsal root ganglia.
10) Place one ganglia in each gel and place at 37C for 1 hr.
11) Add 1 ml of neuronal media to each gel.
12) Change media after 24 hours.

EXAMPLE 3

Degradable Sites in Fusion Protein and In Peptide Chimera NGF fusion proteins containing Factor XIIIa substrate and a Plasmin degradation site β-NGF fusion proteins were expressed with an exogenous cross-liking substrate that allows the β-NGF fusion proteins to be enzymatically cross-linked to fibrin matrices, which served as the base material for the drug delivery system. A plasmin substrate was placed between the cross-linking substrate and the β-NGF domain in the fusion protein, which served as a degradable linker and allowed β-NGF to be released from the matrix in a form almost identical to its native sequence by enzymatic cleavage. The β-NGF fusion proteins were covalently attached to fibrin by the transglutaminase activity of factor XIIIa and were tested in an in vitro model of nerve regeneration to determine the ability of the delivery system to release active growth factors in response to cell-associated enzymatic activity.

Gene synthesis

Two β-NGF fusion proteins were made by recombinant protein expression. Each protein contained a cross-linking substrate at the N-terminus of the protein that consists of the transglutaminase (TG) factor XIIIa substrate from $\alpha_2$-plasmin inhibitor, NQEQVSPL (SEQ ID NO:23). Each β-NGF fusion protein also contained the native β-NGF sequence at the C-terminus of the protein. One of two plasmin substrates (P) was placed between the cross-linking substrate and the β-NGF domain of the fusion protein, either a functional plasmin substrate (LIK/MKP, where/denotes the cleavage site) or a non-functional plasmin substrate (LINMKP) in which the lysine residue at the cleavage site i the plasmin substrate was changed to an asparigine residue to render the plasmin substrate non-functional. The fusion protein containing a functional plasmin substrate was denoted TG-P-NGF, and the fusion protein containing a non-functional plasmin substrate was denoted TG-P$_i$-NGF.

The protein sequence to expressed is as follows: M*GSSHHHHHHSSGLVPRGSH*MNQEQVSPLPVELPLI-KMKPVELESSSHPI FHRGEFSVCDSVSVWVGD-KTTATDIKGKEVMVLGEVNINNSVFKQYFF-ETKCRDPNPVDSGCRGIDSKHWNSYCTTTHTFVKAL-TMDGKQAAWRFI RIDTACVCVLSRKAVRZ (SEQ ID NO:24), where the region in italics is the Histidine tag derived from the expression vector, and the underlined region is the thrombin cleavage site. The residues are the cross-linking substrate sequence for factor XIIIa, and double underlined region denotes the plasmin substrate.

The cloning plasmid used for gene assembly was pUC 18. The DNA sequence of the gene is as follows from 5' to 3': GAATTCCCATGGCATATGAACCAGGAACAGGTTA-GCCCGCTGCCCGT GGAACTGCCGCTGATCAAAAT-GAAACCCGTGGAACTCGAGAGCTCTT CCCAC- CCGATTTTCCATCGTGGCGAGTTCTCCGTGTGT-
GACTCTGTCT CTGTATGGGTAGGCGATAAAACCAC-
TGCCACTGATATCAAAGGCAAA GAGGTGATGGT-
GCTGGGAGAAGTAAACATTAACAACTCT-
GTATTCAA ACAGTACTTCTTCGAAACTAAGTGC-
CGTGACCCGAACCCGGTAGACT CTGGGTGTC-
GCGGCATCGATTCTAAACACTGGAACTCTTACTG-
CACC ACTACTCACACTTTCGTTAAAGCGT-
TGACTATGGATGGTAAACAGGC TGCCTGGCGTTT-
CATCCGTATCGATACTGCATGCGTGTGTGTACTGTC
CCGTAAAGCTGTTCGTTAAGGATCC (SEQ ID NO:25).

In order to synthesize the β-NGF fusion protein by recombinant protein expression, the gene coding for the protein was cloned. Once the gene fragments were designed, Eco RI and Hind III sites were added to the end of each fragment, to allow the cloning of these fragments into the poly-cloning linker of pUC18 (Gibco, Basel, Switzerland). The 3' and 5' single-stranded oligonucleotides of each gene fragment were synthesized by Microsynth (Balgach, Switzerland) with sticky ends for the two cloning restriction sites. The single-stranded oligonucleotides were purified using denaturing poly-acrylamide gel electrophoresis (PAGE), the highest molecular weight band for each fragment was extracted from the gel, and the corresponding 3' and 5' oligonucleotide fragments were annealed. The annealed fragments were phosphorylaed with T4 DNA kinase (Boehringer Mannheim, Rotkreuz, Switzerland) and ligated into pUC18. Following ligation, the plasmids were transformed into DH5α-F' competent cells and plated on isopropyl β-D-thiogalactopyranoside (IPTG)/5-bromo-4-chloro-3-indolyl β-D-galactopyranoside (X-gal)/ampicillin (Amp) plates to screen for insertion of the gene fragments into the plasmids. Plasmids from colonies containing inserted gene fragments were sequenced to identify colonies containing gene fragments with the correct sequence. After the correct sequence for each gene fragments was obtained, the fragments were assembled to form the complete gene for the fusion protein. Briefly, plasmids that contained fragment 2 were digested with the enzymes EcoR V and Hind III (Boehringer Mannheim), and the fragments was purified by non-denaturing PAGE. Plasmids containing fragment 1 were digested with the enzymes Eco RV and Hind III, dephosphorylated with alkaline phosphatase (Boehringer Mannheim), and the digested plasmids were purified by agarose gel electrophoresis. Fragment 2 was ligated into the digested plasmids that contained fragment 1 to obtain a plasmid that contained both fragments 1 and 2. This plasmid was transformed into DH5α-F' competent cells, and plated on Amp plates. The resulting colonies were screened for plasmids containing both fragments, and these plasmids were sequenced. This process was repeated until the complete gene for the β-NGF fusion protein was assembled.

The gene for the TG-P$_i$-NGF fusion protein was made from the TG-P-NGF gene by site directed mutagenesis. Polymerase chain reaction (PCR) was performed to modify the region of the fusion protein gene coding for the plasmin substrate, using primers containing the desired modification of the gene. Using the TG-P-NGF gene as a template, two reactions were performed, one with primer A and primer B, and the other with primer C and primer D.
Primer A AACAGCTATG ACCATG (M13 reverse)
Primer B GTTTCATGTT GATCAGCGGC AGT
Primer C TGATCAACAT GAAACCCGTG GAA
Primer D GTAAAACGACG GCCAGT (M13)
(SEQ ID NO:26–29) The products from the two reactions were purified by agarose gel electrophoresis, and used as primers for the third reaction. Primers A and D were also added to the third reaction to amply the desired product. The final reaction product was digested with Eco RI and Hind III and purified by agarose gel electrophoresis. The PCR fragment was cloned into pCU18, and sequenced to identify the correct PCR product.

Protein Expression

The complete gene for each of the β-NGF fusion proteins was digested out of pUC18 and ligated into the expression vector, pET14B (Novgaen, Madison, Wis.). The expression vector was transformed into the expression host, BL21 (DE3) pLysS to allow for tight regulation of fusion protein expression. The fusion protein was expressed by growing the E. coli until they reached mid-log phase growth (optical density at 600 nm of 0.4–0.6) and then inducing protein expression by the addition of 0.4 mM IPTG to the culture medium. The bacteria were harvested after 2 hr by centrifugation at 5500xg. After harvesting, the cells were suspended in ⅒ the culture volume of 20 mM Tris HCl, 250 mM NaCl, pH 8.0. Lysozyme (0.4 mg/mL) and DNase (5 ng/mL) wee added to the harvested cells, and the solution was incubated at 37° C. for 30 minutes. The inclusion bodies were collected from the cell lysate by centrifugation at 10,000 x g for 15 min. The pellet containing the inclusion bodies was resuspended in 40 mL/liter culture volume of binding buffer (5 mM imidazole, 0.5 M NaCl, 20 mM Tris HCl, pH 7.9) containing 6 M guanidine hydrochloride (GuHCl) at room temperature for 90 min. Insoluble material in the solution was collected by centrifugation for 20 min at 20,000 x g, and the supernatant, which contained the solubilized fusion protein, was saved for further purification.

Protein Purification

The fusion protein contained a thrombin-cleavable histidine tag for purification at the N-terminus of the protein, because the gene for the β-NGF fusion protein was inserted in pET14b between the Nde I and Bam HI sites. Nickel affinity chromatography was used to purify the β-NGF fusion protein. His Bind™ resin (Novagen) was packed into a chromatography column (2.5 mL bed volume per liter culture volume), charged with Ni$^{++}$ and equilibrated with binding buffer containing 6 M GuHCl (according to the manufacturer's instructions). The supernatant, which contained the fusion protein, was filtered with a 5 μm syringe filter and loaded on the column. The column was washed with 10 column volumes of binding buffer containing 8 M urea and 6 column volumes of wash buffer (20 mM imidazole, 0.5 M NaCl, 20 mM Tris HCl, pH 7.9) containing 8 M urea. The fusion protein was eluted with 4 column volumes of elution buffer (1 M imidazole, 0.5 M NaCl, 20 mM Tris HCl, pH 7.9) containing 8 M urea. The presence of β-NGF fusion protein in the elution fractions was confirmed by sodium dodecyl sulfate (SDS)-PAGE.

Protein Refolding

The β-NGF fusing protein was reflected by adding a 5-fold excess of ice cold refolding buffer (20 mM Tris HCl, 250 mM NaCl, 2 mM reduced glutathinone and 0.2 mM oxidized glutathinone, pH 8.0) to the purified β-NGF fusion protein slowly, until a final urea concentration of 1.3 M was attained. The fusion protein was refolded for 48 hr at 4° C. while stirring. The reflected fusion protein was dialyzed against a 50-fold excess of storage buffer (20 mM Tris HCl, 500 mM NaCl, pH 8.0) containing 10% glycerol at 4° C. overnight. The function protein was concentrated by centrifugation using Vivaspin™ concentrators (5000 MW cutoff, Vivascience, Lincoln, UK) to a concentration of about 300–400 μg/mL, as measured by Bradford assay.

Incorporation of β-NGF Fusion Protein into Fibrin Matrices

To determine the efficiency of β-NGF fusion protein incorporation into fibrin matrices, TG-P$_i$-NGF fusion protein was labeled with biotin to allow β-NGF quantification by a direct enzyme-linked immunosorbent assay (ELISA). A 20-fold molar excess of Sulfo-N-hydroxysuccinimide (NHS)-LC Biotin (Pierce, Lausanne, Switzerland) was added to the β-NGF fusion protein in phosphate buffered saline (PBS, 0.01 M phosphate buffer, 8 g/L NaCl, 0.2 g/L KCl, pH 7.4) at a concentration of 1 mg/mL from a stock solution of 10 mg/mL biotin in N,N-dimethylformamide (dissolved for 10 min at 37° C.). The reaction was allowed to proceed for 2 hr at room temperature. The unreacted biotin was then removed by gel filtration chromatography using a PD-10 column (Amersham Pharmacia, Dubendorf, Switzerland).

A known amount of labeled β-NGF was adsorbed to 96 well plates overnight in coating buffer (0.1 M NAHCO$_3$, pH 8) at 4° C. The wells were blocked with 1% bovine serum albumin (BSA) in PBS for 2 hr at room temperature. The wells were washed 3 times in PBS with 0.5% Tween-20 (PBST buffer). Horse radish peroxidase (HRP)-conjugated streptavidin was diluted to 1 μg/mL in PBS and added to each well for 1 hr. The wells were washed 3 times with PBST buffer and then incubated in ABTS (2,2'-Azino-bis (3-ethylbenz-thiazoline-6-sulfonic acid)) developing solution (0.1M NaC$_2$H$_3$O$_2$, 0.05 M NaH$_2$PO$_4$, 0.1% ABTS, 0.01% H$_2$O$_2$, pH 4.2). After 1–5 minutes, the reaction was stopped by adding an equal volume of 0.6% SDS, and the absorbance of each well was measured at 405 nm using an EL311SX plate reader from Bio-Tek Instruments (Winooski, Vt.). A standard curve of β-NGF concentration versus absorbance at 405 nm was made using these measurements from the direct ELISA assay.

Plasminogen-free fibrinogen was dissolved in water and dialyzed versus Tris-buffered saline (TBS, 33 mM Tris, 8 g/L NaCl, 0.2 g/L KCl) at pH 7.4 for 24 hr. β-NGF fusion protein was incubated with 5 mM Ca$^{++}$ and 4 NIH units/mL thrombin for 1 hr at 37° C. to remove the histidine tag used for purification. The β-NGF fusion protein solution was mixed in equal ratio with fibrinogen at a concentration of 8 mg/mL and polymerized at 37° C. for 60 min. The fibrin matrices were washed 5 times over 24 hr, and each wash was saved to determine the total amount of β-NGF washed out of the matrix. After 24 hr, the fibrin matrices containing β-NGF wee degraded with 0.1 U of porcine plasmin. The amount of β-NGF in the washes and remaining in the matrix was quantified as described above by direct ELISA, and a β-NGF standard curve was constructed for each ELISA performed.

A Western blot was performed to show directly the β-NGF fusion proteins were covalently coupled to fibrin matrices. Fibrin matrices were made and washed as described in the incorporation quantification assay. The matrices were washed 5 times over 24 hr and then degraded with plasmin, as described above. The degradation products were separated by SDS-PAGE using a 13.5% denaturing gel. The proteins from the gel were transferred to an activated Immobilon-P™ polyvinlidene difluoride (PVDF) membrane (Millipore, Volketswil, Switzerland) with a current of 400 mA for 1 hr. The membrane was dried overnight. The proteins transferred to the membrane, including the molecular weight marker, were visualized by straining with 0.2% Pronceau S. Non-specific protein binding to the membrane was blocked with 3% BSA in TBS for 2 hr. The membrane was incubated with goat anti-human β-NGF antibody (R&D Systems, Minneapolis, Minn.) at a concentration of 0.2 μg/mL in 3% BSA for 1 hr. The membrane was washed 3 times with TBS for 5 min and incubated with the secondary antibody, HRP-conjugated rabbit anti-goat immunoglobins (Dako Diagnostics, Zug, Switzerland) at a concentration of 0.5 μg/mL in 3% BSA for 30 min. The membrane was washed 3 times with TBS, and then incubated for 5 min with an enhanced chemi-luminescent HRP substrate (pierce, Lausanne, Switzerland) diluted 1:5 in TBS. Excess liquid was removed from the membrane and it was covered with plastic and was exposed to X-ray film for 5–60 sec.

An increase in molecular weight was indeed observed for β-NGF fusion proteins that were present during polymerization of fibrin matrices), while in the case of β-NGF lacking a cross-linking substrate, no β-NGF was observed in the matrix after washing. This result showed directly that the β-NGF fusion protein was covalently immobilized within fibrin matrices during polymerization via the transglutaminase activity of factor XIIIa.

Bioactivity of Immobilized β-NGF fusion Protein

Figure 3:
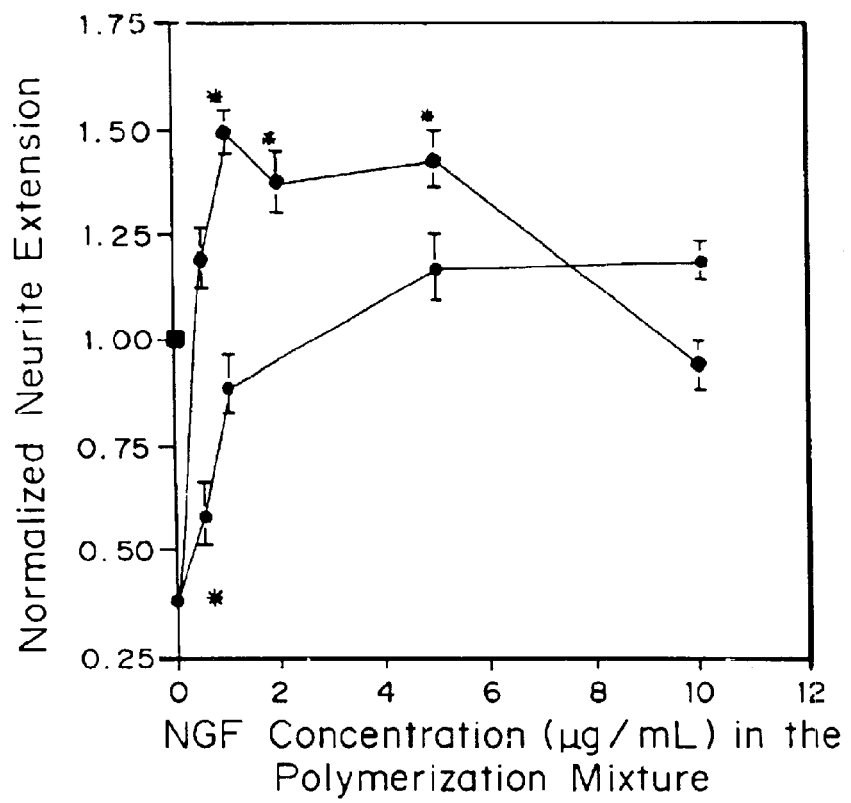
FIG. 3 is a graph of the effect of immobilized β-nerve growth factor (NGF) fusion proteins on DRG neurite extension with fibrin matrices. Mean values and standard error of the means are shown. ■ denotes native NGF. ♦ denotes TG-P-NGF. ● denotes TG-P$_i$-NGF. * denotes p<0.0001 versus unmodified fibrin with NGF in the culture medium. This result demonstrates that matrix-bound β-NGF enhances neurite extension through fibrin matrices versus the same concentration of NGF in the medium.

To determine the ability of covalently immobilized β-NGF fusion protein to be delivered in a controlled manner, β-NGF fusion proteins were incorporated into fibrin matrices during polymerization, and the ability of these matrices to enhance neurite extension in vitro was assayed using chick DRGs. TG-P-NGF was found to enhance neurite extension by over 350% versus unmodified fibrin with no NGF present in the culture medium and by up to 50% over unmodified fibrin with 10 ng/mL of native NGF in medium (FIG. 3). TG-P$_i$-NGF, which contained a non-functional plasmin substrate, could not be cleaved from the fibrin matrix by plasmin in a native form and did not significantly enhance neurite extension versus native NGF in the culture medium, when covalently immobilized within fibrin matrices at any of the concentrations tested. However, TG-P-NGF, which contained a functional plasmin substrate, could be cleaved from the matrix by plasmin in a form very similar to native NGF and was observed to enhance neurite extension, even when compared with similar doses of native NGF present in the culture medium. A dose response effect for TG-P-NGF fusion protein was observed, with an optimal dose attained when 1–5 μg/mL of β-NGF fusion protein was present in the polymerization mixture. These results demonstrated that the TG-P-NGF fusion protein was bioactive when immobilized within fibrin matrices, suggesting that it could be released in an active form by cell-associated matrix degradation. Despite the lower activity of the β-NGF fusion proteins in the PC12 cell activity assay, when the plasmin degradable β-NGF fusion protein was covalently coupled to fibrin, it promoted greater levels of neurite extension than the same dose of native NGF in the culture medium. These results also suggested that for the β-NGF fusion proteins to be fully active, they must be release from the fibrin matrix in a form similar to that of their native structure.

Efficiency of β-NGF Fusion Protein Cross-linking

Figure 4:
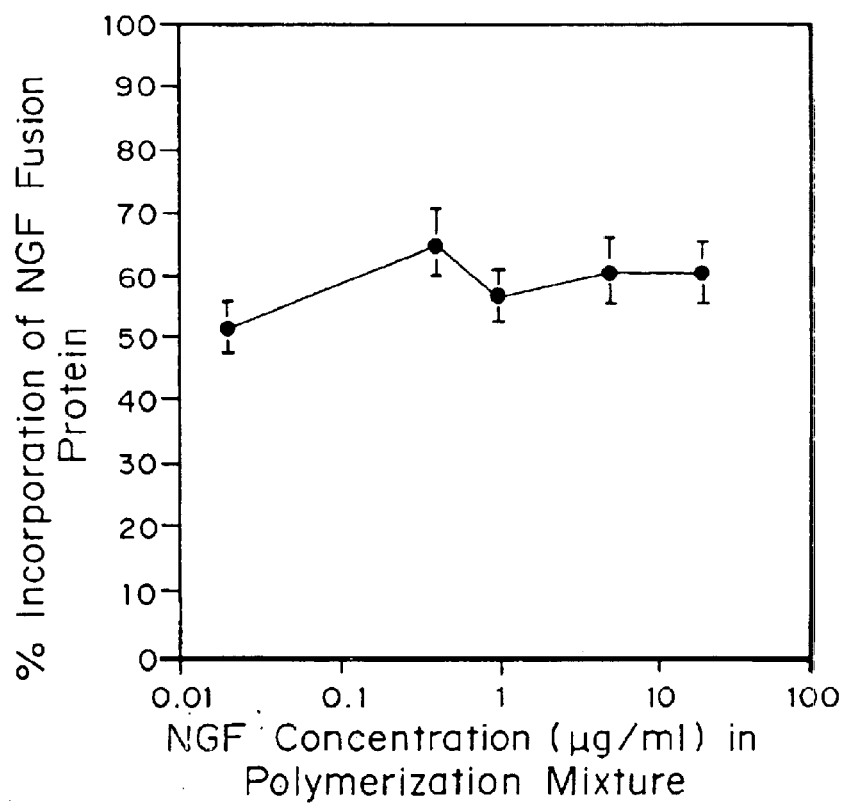
FIG. 4 is a graph of the amount of incorporation of β-NGF fusion protein with exogenous factor XIIIa substrate into fibrin matrices, quantified by direct ELISA, using biotin-labeled β-NGF. The incorporation efficiency of the β-NGF fusion protein was relatively constant over the range of concentrations tested.

To determine the efficiency of β-NGF fusion protein incorporation in fibrin matrices, the protein was labeled with biotin, and a direct ELISA was performed on fibrin matrices that contained biotin-labled β-NGF fusion protein in the polymerization mixture. Biotin-labeled β-NGF fusion proteins were incorporated into fibrin matrices during polymerization. After washing to remove any unbound β-NGF fusion protein, the matrices were degraded with plasmin and the amount of β-NGF in the degraded matrices and in the washes was quantified. The percentage of β-NGF fusion protein incorporated into the fibrin matrix is shown in FIG. 4 as a function of β-NGF concentration in the polymerization mixture. Over the range β-NGF fusion protein concentrations tested, 50–60% of the fusion protein was incorporated during polymerization of the fibrin matrix. This result demonstrated that β-NGF fusion proteins were incorporated into fibrin matrices efficiently through the action of factor XIIIa.

β-NGF fusion protein with a heparin binding domain and a plasma degradation site NGF can be expressed as fusion protein in *E. coli*, which contains a heparin-binding domain at the N-terminus, a plasmin substrate in the middle and the NGF sequence at the C-terminus of the protein. This is accomplished by constructing a synthetic gene containing the DNA which codes for the desired fusion protein. The protein sequence to expressed is as follows: MGSS*HHHHHH*SSG LVPRGSHMKDPKRLYRSRKLPVELPLIKMKPVELESS SHPIFHRGEFSVCDSVSVWVGDKTTATDIKGKEV-MVLGEVNINNSVFKQ YFFETKCRDPNPVDSGCR-GIDSKHWNSYCTTTHTFVKALTMDGKQAAW RFIRI-DTACVCVLSRKAVRZ (SEQ ID NO:30), where the region in italics is the Histidine tag derived from the expression vector, and the underlined region is the thrombin cleavage site. Dotted underline denote the heparin-binding sequence, and double underline denotes the plasmin substrate.

The cloning plasmid used for gene assembly was pUC 18. The DNA sequence of the gene is as follows from 5' to 3': GAATTCCCATGGCATATGAAAGACCCGAAACGTC-TGTACCGTTCTCG TAAACTGCCCGTGGAACTGC-CGCTGATCAAAATGAAACCCGTGGAAC TCGAG-AGCTCTTCCCACCCGATTTTCCATCGTGGCGA-GTTCTCCGTGT GTGACTCTGTCTCTGTATGGGTAG-GCGATAAAACCACTGCCACTGAT ATCAAAG-GCAAAGAGGTGATGGTGCTGGGAGAAG-TAAACATTAACA ACTCTGTATTCAAACAGTACT-TCTTCGAAACTAAGTGCCGTGACCCG AACCCGG-TAGACTCTGGGTGTCGCGGCATCGATTCTAAACA-CTGGAA CTCTTACTGCACCACTACTCACA-CTTTCGTTAAAGCGTTGACTATGGA TGGTAAACA-GGCTGCCTGGCGTTTCATCCGTATCGATACTGC-ATGCG TGTGTACTGTCCCGTAAAGCTGT-TCGTTAAGGATCC (SEQ ID NO:31).

This gene is inserted between the EcoRI and HindIII sites in the polylinker cloning region of pUC 18, a shown in the map.

After assembly this gene is inserted into the expression vector. Expression and purification are then performed as described above.

EXAMPLE 4

Fusion Proteins of growth factors that do bind heparin spontaneously.

A. Biosynthesis of Factor XIIIa substrate fusion proteins with NGF

NGF can be expressed as fusion protein in *E. coli*, which contains a factor XIIIa substrate at the N-terminus and the human β-NGF sequence at the C-terminus of the protein. This is accomplished by constructing a synthetic gene containing the DNA which codes for the desired fusion protein. The protein sequence to expressed is as follows: MGSS*HHHHHH*SSGLVPRGSHMNQEQVSPLPVELES-SSHPIFHRGEFSVCD SVSVWVGDKTTATDIKGKEVM-VLGEVNINNSVFGQYFFETKCRDPNPV DSGCRGI-DSKHWNSYCTTTHTFVKALTMDGKQAAWRFIRID-TACVCVL SRKAVRZ (SEQ ID NO:32), where the region in italics is the Histidine tag derived from the expression vector, and the underlined region is the thrombin cleavage site. The residues are the cross-linking substrate sequence for factor XIIIa.

The cloning plasmid used for gene assembly was pUC 18, which is the same as pUC 19 except that the sequence of the polylinker cloning region is reversed. A map of pUC 19 follows, which was obtained from New England Biolabs. The DNA sequence of the gene is as follows from 5' to 3': GAATTCCATATGAACCAGGAACAGGTTAGCC-CGCTGCCCGTGGAACT CGAGAGCTCTTCCCAC-CCGATTTTCCATCGTGGCGAGTTCTCCGTGTG TGACTCTGTCTCTGTATGGGTAGGCGATAAAAC-CACTGCCACTGATA TCAAAGGCAAAGAGGTGATG-GTGCTGGGAGAAGTAAACATTAACAA CTCTGTA-TTCAAACAGTACTTCTTCGAAACTAAGTCCG-TGACCCGA ACCCGGTAGACTCTGGGTGTCGCG-GCATCGATTCTAAACACTGGAAC TCTTACTGCACC-ACTACTCACACTTTCGTTAAAGCGTTGACTATGGAT GGTAAACAGGCTGCCTGGCGTTTCATCCGTAT-CGATACTGCATGCGT GTGTACTGTCCCG-TAAAGCTGTTCGTTAAGGATCC (SEQ ID NO:33).

This gene is inserted between the EcoRI and HindIII sites in the polylinker cloning region of pUC 18, shown in the map. After gene assembly, this gene is inserted into the expression vector pET 14b between the NdeI and BamHI sites. A map of the pET 14b vector follows, which was obtained from Novagen. After insertion of the gene into the expression vector, the plasmid is transformed into BL21 (DE3)pLysS component cells. The cell are grown until they reach an OD of about 0.6, then they are induced to express of the fusion protein with IPTG (final concentration in solution 0.4 mM). Expression is continued for 2–3 hours. The cells are placed on ice for 5 minutes and then harvested by centrifugation at 5000 x g for 5 min. at 4° C. They are resuspended in 0.25 culture volume of cold 50 mM Tris-HCl pH 8.0 at 25C. The cells are centrifuged as before and the pellet is frozen. Cells are lysed upon thawing.

The cell lysate is centrifuged and the supernatant discarded. The pellet is resuspended in Triton X100. The solution is then centrifuged and the supernatant is discarded. The pellet is resuspended in 6M urea and the fusion protein is purified by histidine affinity chromatography. The histidine tag can be cleaved by thrombin during polymerization and washed from the gels during the standard washing procedure.

B. Biosynthesis of heparin-binding domain fusion proteins of NGF

NGF can be expressed as fusion protein in *E. coli*, which contains a heparin-binding domain at the N-terminus and the NGF sequence at the C-terminus of the protein. This is accomplished by constructing a synthetic gene containing the DNA which codes for the desired fusion protein. The protein sequence to expressed is as follows: MGSS*HHH-HHH*SSGLVPRGSHMKDPKRLYRSRKLPVELESSSHPI-FHRGEF SVCDSVSVWVGDKTTATDIKGKEVMVL-GEVNINNSVFKQYFFETKCRD PNPVDSGCRGIDSKH-WNSYCTTTHTFVKALTMDGKQAAWRFIRIDTAC VCVLSRKAVRZ (SEQ ID NO:34). where the region in italics is the Histidine tag derived from the expression vector, and the underlined region is the thrombin cleavage site. The region underlined with a dotted underline is the heparin-binding sequence.

The cloning plasmid used for gene assembly was pUC 18. The DNA sequence of the gene is as follows from 5' to 3': GAATTCCCATGGCATATGAAAGACCCGAAACG-TCTGTACCGTTCTCG TAAACTGCCCGTGGAACTC-GAGAGCTCTTCCCACCCGATTTTCCATCG TGGCGAGTTCTCCGTGTGTGACTCTGTCTCTGTA-TGGGTAGGCGATAA AACCACTGCCACTGATAT-CAAAGGCAAAGAGGTGATGGTGCTGGGA GAAGTAAACATTAACAACTCTGTATTCAAACAGTA-CTTCTTCGAAAC TAAGTGCCGTGACCCGAACCCG-GTAGACTCTGGGTGTCGCGGCATCGA TTCTA-AACACTGGAACTCTTACTGCACCACTACTCACACT-TTCGTTA AAGCGTTGACTATGGATGGTAAACAG-GCTGCCTGGCGTTTCATCCGT ATCGATACTGCAT-GCGTGTGTGTACTGTCCCGTAAAGCTGTTCGTTAA GGATCC (SEQ ID NO:35).

This gene is inserted between the EcoRI and HindIII sites in the polylinker cloning region of pUC 18, as shown in the map. After assembly this gene is inserted into the expression vector. Expression and purification are then performed as described above.

EXAMPLE 5

BMP2 Delivery from Fibrin matrices with Bi-domain peptides for Heparin Affinity.

It has been demonstrated that bone morphogenetic factor bound to the fibrin matrix is able to control the release of this factor and when this matrix is implanted subcutaneously ectopic bone is formed. While hits procedure is different from bone formation within a bony defect, it does provides a suitable method for testing the ability to control the release of a bioactive growth factor in vivo.

Fibrin gels were synthesized with a different bi-domain peptide with the sequence LNQEQVSPK(A)FAKLAARLYRKA (SEQ ID NO:36). This peptide is derived from the Factor XIIIa substrate sequence for 2-plasmin inhibitor in the first domain and a mimetic of the heparin binding domain of antithrombin III in the second domain. BMP-2 is a heparin binding protein and will bind to the sequence given above. Gels were polymerized in the presence of the peptide (at 1 mM), heparin and recombinant human BMP-2 in ratios of heparin to BMP-2 of 1:1 and 40:1.

Control gels were created that had equivalent amounts of the morphogenetic protein, BMP-2, but lacking the heparin and bi-domain peptide. These gels were then implanted subcutaneously into rats and were allowed to remain for two weeks. When the matrices were extracted little to no bone was observed from the gels that did not contain the peptide-heparin release system while the gels that did contain the system showed significant bone formation.

This is best seen in the mass of the removed matrices which is shown in Table 3.

| Treatment | Explanted Matrix (mg ± s.e.m.) |
|---|---|
| Fibrin + 20 microgram BMP-2 | 7.4 ± 6.5 |
| Fibrin + 1 mMol peptide + 26 microgram heparin + 20 microgram BMP-2 | 34.5 ± 25.5 |
| Fibrin + 1 mMol peptide + 1 mg heparin + 20 microgram BMP-2 | 39.2 ± 20.8 |

The release system enhanced the formation of ectopic bone within the matrix, demonstrating the viability of the release system in vivo.

EXAMPLE 6

Incorporation of Peptide with exogenous Factor XIII.

Purified fibrinogen as obtained via standard precipitation methods contains small amounts of endogenous factor XIIIa which act as a limiting reagent in the incorporation of the bi-domain peptide. This was demonstrated using purified fibrinogen, in which it was possible to incorporate the bi-domain peptides at concentrations up to 8.2 mol peptide/mol fibrinogen based on the endogenous factor XIIIa concentration. Addition of exogenous factor XIIIa was demonstrated to enhance the level of peptide incorporation. This is particularly relevant for control of the bi-domain peptide concentration within the gel, which in turn will affect both cell adhesion as well as determine the upper limit for heparin and growth factor incorporation. In some cases it may be advantageous to increase cellular adhesion, heparin, or growth factor concentrations beyond that possible with standard purified fibrinogen.

Figure 5:
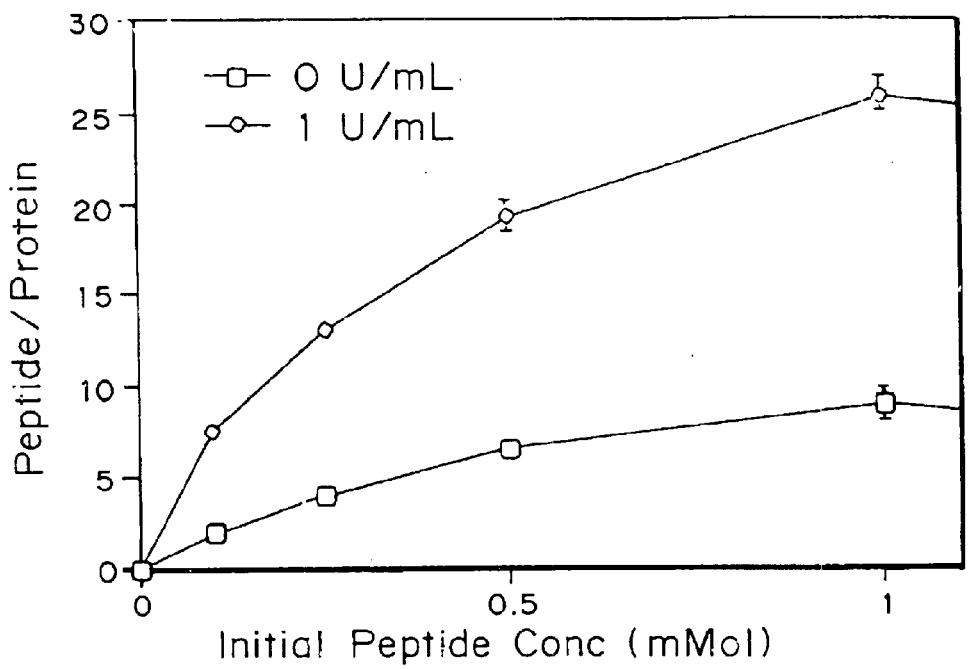
FIG. 5 is a graph of the incorporation of dLNQEQVS-PLRGD (SEQ ID NO:1) into fibrin gels with exogenous Factor XIII added. When 1 U/mL was added, the level of incorporation increased such that more than 25 mol peptide/mol fibrinogen could be achieved.

Exogenous factor XIII, purified from pooled plasma, was used to incorporate the bidomain peptide, dLNQEQVSPL-RGD (SEQ ID NO:1), into the gels, 1 U of exogenous factor XIII was added per mL fibrin gel, and the level of covalently incorporated bi-domain peptide analyzed through chromatographic analysis. The results are shown in FIG. 5. When 1 U/mL of exogenous Factor XIII was added the level of incorporation reaching 25 mol peptide/mol fibrinogen. This level of incorporation is close to the theoretical limit based on the number of possible binding sites.

Figure 6:
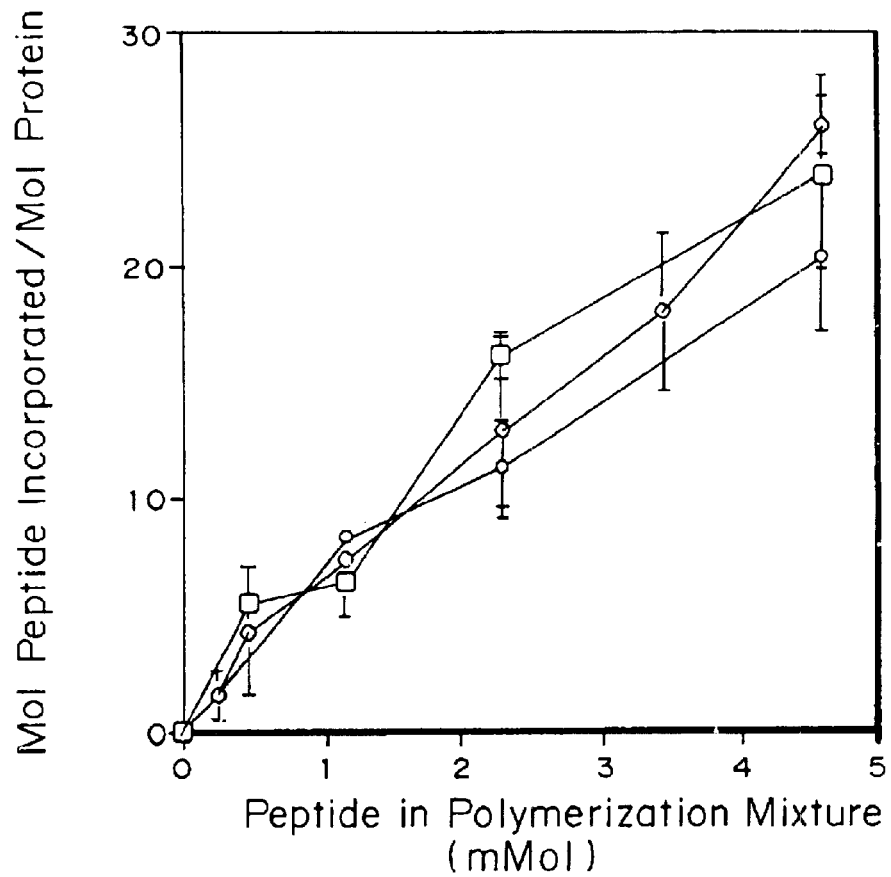
FIG. 6 is a graph of the incorporation of the bidomain peptide, dLNQEQVSPLRGD (SEQ ID NO:1) into undiluted fibrin glue. Three separate kits were tested and in each case a high level of incorporation could be observed, reaching 25 mol peptide/mol fibrinogen. The concentration of exogenous peptide required for maximal incorporation was at least 5 mM, possibly due to diffusion limitations within the highly dense fibrin matrix that is created. The level of incorporation was very consistent, with each kit providing a similar incorporation profile.

The ability of the bi-domain peptide, dLNQEQVSPL-RGD (SEQ ID NO:1), to incorporate into commercially available fibrin glue kits was also demonstrated. Tissucol kits were obtained and then fractionated into multiple samples. Exogenous bi-domain peptide was added at up to 6 mM and the level of incorporation was measured through chromatographic analysis (FIG. 6). The level of peptide incorporation was tested over a wide range of initial bi-domain peptide concentrations for three separate kits. When the level of incorporation was measured, it was observed that the maximal incorporation occurred at concentrations of greater than 5 mM exogenous peptide. It may be that in these highly dense matrices, diffusion begins to play a role in the process of incorporation. However, a very high level of incorporation was observed with the level reaching at least 25 mol peptide/mol fibrinogen. Furthermore, there is a significant variability in the composition of fibrin glue kits with a wide range of possible protein concentrations present. However, this clearly did not affect the incorporation of the bi-domain peptide significantly as the incorporation profile was similar for all three kits tested.

Modifications and variations of the present invention will be obvious to those skilled in the art from the foregoing detailed description and are intended to be encompassed by the following claims.

What is claimed is:

1. An engineered protein or polysaccharide comprising at least one first domain comprising heparin or heparin-like peptides, and a second attachment domain, wherein the second domain is a substrate domain for a crosslinking enzyme, and wherein the engineered protein or polysaccharide is covalently attachable to a matrix through the second attachment domain.

2. The engineered protein or polysaccharide of claim 1, wherein the second attachment domain comprises a transglutaminase substrate domain.

3. An engineered protein or polysaccharide comprising at least one first domain comprising heparin or heparin-like peptides, and a second attachment domain, and a cleavage site between the first domain and the second attachment domain, wherein the engineered protein or polysaccharide is covalently attachable to a matrix through the second attachment domain.

4. The engineered protein or polysaccharide of claim 3, wherein the cleavage site is an enzymatic cleavage site, which is cleaved by an enzyme selected from the group consisting of plasmin and matrix metalloproteinase.

5. The engineered protein or polysaccharide of claim 2 wherein the second attachment domains is a Factor XIIIa substrate domain.

6. The engineered protein or polysaccharide of claim 5 wherein the second attachment domain comprises SEQ ID NO:20.

* * * * *

SEQUENCE LISTING

<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: bidomain
      peptide
<221> NAME/KEY: MOD_RES
<222> LOCATION: (1)
<223> OTHER INFORMATION: dansyl Leucine

<400> SEQUENCE: 1

Leu Asn Gln Glu Gln Val Ser Pro Leu Arg Gly Asp
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Substrate
      Sequence for Protease

<400> SEQUENCE: 2

Leu Ile Lys Met Lys Pro
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Substrate
      Sequence for Protease

<400> SEQUENCE: 3

Asn Phe Lys Ser Gln Leu
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Substrate
      Sequence for Protease
<221> NAME/KEY: MOD_RES
<222> LOCATION: (1)
<223> OTHER INFORMATION: Acetylated Glycine

<400> SEQUENCE: 4

Gly Pro Leu Ala Leu Thr Ala Leu
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Substrate
      Sequence for Protease
<221> NAME/KEY: MOD_RES
<222> LOCATION: (1)
<223> OTHER INFORMATION: Acetylated Proline
<223> OTHER INFORMATION: C-terminal Amide

```
<400> SEQUENCE: 5

Pro Phe Glu Leu Arg Ala
  1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Substrate
      Sequence for Protease
<221> NAME/KEY: MOD_RES
<222> LOCATION: (1)
<223> OTHER INFORMATION: Carboxybenzoyl group
<223> OTHER INFORMATION: C-terminal Amide

<400> SEQUENCE: 6

Ala Ala Phe Ala
  1

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Substrate
      Sequence for Protease

<400> SEQUENCE: 7

Gly Pro Leu Gly Ile Ala Gly Pro
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Substrate
      Sequence for Protease

<400> SEQUENCE: 8

Pro His Tyr Gly Arg Ser Gly Gly
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Substrate
      Sequence for Protease

<400> SEQUENCE: 9

Pro Gly Ser Gly Arg Ser Ala Ser Gly
  1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:
      Heparin-binding sequence
<221> NAME/KEY: MOD_RES
<222> LOCATION: (2)
<223> OTHER INFORMATION: bAla      beta Alanine

<400> SEQUENCE: 10
```

```
Lys Ala Phe Ala Lys Leu Ala Ala Arg Leu Tyr Arg Lys Ala
 1               5                  10
```

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 11
```

```
Tyr Lys Lys Ile Ile Lys Lys Leu
 1               5
```

```
<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 12
```

```
Lys His Lys Gly Arg Asp Val Ile Leu Lys Lys Asp Val Arg
 1               5                  10
```

```
<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 13
```

```
Tyr Glu Lys Pro Gly Ser Pro Pro Arg Glu Val Val Pro Arg Pro Arg
 1               5                  10                  15

Pro Cys Val
```

```
<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 14
```

```
Lys Asn Asn Gln Lys Ser Glu Pro Leu Ile Gly Arg Lys Lys Thr
 1               5                  10                  15
```

```
<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 15
```

```
Lys Asp Pro Lys Arg Leu
 1               5
```

```
<210> SEQ ID NO 16
<211> LENGTH: 6
<212> TYPE: PRT
```

```
<213> ORGANISM: Artificial Sequence
<220> FEATURE:
<223> OTHER INFORMATION: Description of Artificial Sequence:
      Heparin-binding sequence

<400> SEQUENCE: 16

Tyr Arg Ser Arg Lys Tyr
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 17

Tyr Lys Lys Pro Lys Leu
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 18

Ala Lys Arg Ser Ser Lys Met
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:
      Heparin-binding sequence

<400> SEQUENCE: 19

Cys Arg Lys Arg Cys Asn
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Substrate

<400> SEQUENCE: 20

Asn Gln Glu Gln Val Ser Pro
 1               5

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: A peptide
      chimera containing both a factor XIIIa substrate
      and a heparin-binding domain
<221> NAME/KEY: MOD_RES
<222> LOCATION: (1)
<223> OTHER INFORMATION: dansyl Leucine
<221> NAME/KEY: MOD_RES
<222> LOCATION: (10)
```

<223> OTHER INFORMATION: bAla    beta Alanine

<400> SEQUENCE: 21

Leu Asn Gln Glu Gln Val Ser Pro Lys Ala Phe Ala Lys Leu Ala Ala
 1               5                  10                  15

Arg Leu Tyr Arg Lys Ala
             20

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Peptide
<221> NAME/KEY: MOD_RES
<222> LOCATION: (1)
<223> OTHER INFORMATION: dansyl Leucine

<400> SEQUENCE: 22

Leu Asn Gln Glu Gln Val Ser Pro Leu Lys Lys Lys Gly
 1               5                  10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:
      Transglutaminase (TG) factor XIIIa substrate

<400> SEQUENCE: 23

Asn Gln Glu Gln Val Ser Pro Leu
 1               5

<210> SEQ ID NO 24
<211> LENGTH: 163
<212> TYPE: PRT
<213> ORGANISM: Artificial Sequence
<220> FEATURE:
<223> OTHER INFORMATION: Description of Artificial Sequence: Protein
      Sequence

<400> SEQUENCE: 24

Met Gly Ser Ser His His His His His His Ser Ser Gly Leu Val Pro
 1               5                  10                  15

Arg Gly Ser His Met Asn Gln Glu Gln Val Ser Pro Leu Pro Val Glu
             20                  25                  30

Leu Pro Leu Ile Lys Met Lys Pro Val Glu Leu Glu Ser Ser Ser His
         35                  40                  45

Pro Ile Phe His Arg Gly Glu Phe Ser Val Cys Asp Ser Val Ser Val
     50                  55                  60

Trp Val Gly Asp Lys Thr Thr Ala Thr Asp Ile Lys Gly Lys Glu Val
 65                  70                  75                  80

Met Val Leu Gly Glu Val Asn Ile Asn Asn Ser Val Phe Lys Gln Tyr
                 85                  90                  95

Phe Phe Glu Thr Lys Cys Arg Asp Pro Asn Pro Val Asp Ser Gly Cys
             100                 105                 110

Arg Gly Ile Asp Ser Lys His Trp Asn Ser Tyr Cys Thr Thr Thr His
         115                 120                 125

Thr Phe Val Lys Ala Leu Thr Met Asp Gly Lys Gln Ala Ala Trp Arg
     130                 135                 140

Phe Ile Arg Ile Asp Thr Ala Cys Val Cys Val Leu Ser Arg Lys Ala 145         150         155         160
Val Arg Glx

<210> SEQ ID NO 25
<211> LENGTH: 450
<212> TYPE: DNA
<213> ORGANISM: Artificial Sequence
<220> FEATURE:
<223> OTHER INFORMATION: Description of Artificial Sequence: Gene

<400> SEQUENCE: 25

| | | | | | |
|---|---|---|---|---|---|
| gaattcccat | ggcatatgaa | ccaggaacag | gttagcccgc | tgcccgtgga | actgccgctg | 60 |
| atcaaaatga | aacccgtgga | actcgagagc | tcttcccacc | cgattttcca | tcgtggcgag | 120 |
| ttctccgtgt | gtgactctgt | ctctgtatgg | gtaggcgata | aaaccactgc | cactgatatc | 180 |
| aaaggcaaag | aggtgatggt | gctgggagaa | gtaaacatta | caactctgt | attcaaacag | 240 |
| tacttcttcg | aaactaagtg | ccgtgacccg | aacccggtag | actctgggtg | tcgcggcatc | 300 |
| gattctaaac | actggaactc | ttactgcacc | actactcaca | ctttcgttaa | agcgttgact | 360 |
| atggatggta | acaggctgc | ctggcgtttc | atccgtatcg | atactgcatg | cgtgtgtgta | 420 |
| ctgtcccgta | aagctgttcg | ttaaggatcc | | | | 450 |

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 26
aacagctatg accatg                                                     16

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 27
gtttcatgtt gatcagcggc agt                                             23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 28
tgatcaacat gaaacccgtg gaa                                             23

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 29
gtaaaacgac ggccagt                                                    17

-continued

```
<210> SEQ ID NO 30
<211> LENGTH: 167
<212> TYPE: PRT
<213> ORGANISM: Artificial Sequence
<220> FEATURE:
<223> OTHER INFORMATION: Description of Artificial Sequence: Protein
      sequence

<400> SEQUENCE: 30

Met Gly Ser Ser His His His His His Ser Ser Gly Leu Val Pro
  1               5                  10                  15

Arg Gly Ser His Met Lys Asp Pro Lys Arg Leu Tyr Arg Ser Arg Lys
                 20                  25                  30

Leu Pro Val Glu Leu Pro Leu Ile Lys Met Lys Pro Val Glu Leu Glu
             35                  40                  45

Ser Ser Ser His Pro Ile Phe His Arg Gly Glu Phe Ser Val Cys Asp
 50                  55                  60

Ser Val Ser Val Trp Val Gly Asp Lys Thr Thr Ala Thr Asp Ile Lys
 65                  70                  75                  80

Gly Lys Glu Val Met Val Leu Gly Glu Val Asn Ile Asn Asn Ser Val
                 85                  90                  95

Phe Lys Gln Tyr Phe Phe Glu Thr Lys Cys Arg Asp Pro Asn Pro Val
                100                 105                 110

Asp Ser Gly Cys Arg Gly Ile Asp Ser Lys His Trp Asn Ser Tyr Cys
            115                 120                 125

Thr Thr Thr His Thr Phe Val Lys Ala Leu Thr Met Asp Gly Lys Gln
        130                 135                 140

Ala Ala Trp Arg Phe Ile Arg Ile Asp Thr Ala Cys Val Cys Val Leu
145                 150                 155                 160

Ser Arg Lys Ala Val Arg Glx
                165

<210> SEQ ID NO 31
<211> LENGTH: 462
<212> TYPE: DNA
<213> ORGANISM: Artificial Sequence
<220> FEATURE:
<223> OTHER INFORMATION: Description of Artificial Sequence: Gene

<400> SEQUENCE: 31
gaattcccat ggcatatgaa agacccgaaa cgtctgtacc gttctcgtaa actgcccgtg      60
gaactgccgc tgatcaaaat gaaacccgtg gaactcgaga gctcttccca cccgattttc     120
catcgtggcg agttctccgt gtgtgactct gtctctgtat gggtaggcga taaaaccact     180
gccactgata tcaaaggcaa agaggtgatg gtgctgggag aagtaaacat taacaactct     240
gtattcaaac agtacttctt cgaaactaag tgccgtgacc cgaacccggt agactctggg     300
tgtcgcggca tcgattctaa acactggaac tcttactgca ccactactca cactttcgtt     360
aaagcgttga ctatggatgg taaacaggct gcctggcgtt tcatccgtat cgatactgca     420
tgcgtgtgtg tactgtcccg taaagctgtt cgttaaggat cc                        462

<210> SEQ ID NO 32
<211> LENGTH: 153
<212> TYPE: PRT
<213> ORGANISM: Artificial Sequence
<220> FEATURE:
<223> OTHER INFORMATION: Description of Artificial Sequence: Protein
      Sequence

<400> SEQUENCE: 32
```

```
Met Gly Ser Ser His His His His His Ser Ser Gly Leu Val Pro
 1               5                  10                  15

Arg Gly Ser His Met Asn Gln Glu Gln Val Ser Pro Leu Pro Val Glu
                20                  25                  30

Leu Glu Ser Ser Ser His Pro Ile Phe His Arg Gly Glu Phe Ser Val
            35                  40                  45

Cys Asp Ser Val Ser Val Trp Val Gly Asp Lys Thr Thr Ala Thr Asp
 50                  55                  60

Ile Lys Gly Lys Glu Val Met Val Leu Gly Glu Val Asn Ile Asn Asn
 65                  70                  75                  80

Ser Val Phe Lys Gln Tyr Phe Phe Glu Thr Lys Cys Arg Asp Pro Asn
                85                  90                  95

Pro Val Asp Ser Gly Cys Arg Gly Ile Asp Ser Lys His Trp Asn Ser
                100                 105                 110

Tyr Cys Thr Thr Thr His Thr Phe Val Lys Ala Leu Thr Met Asp Gly
            115                 120                 125

Lys Gln Ala Ala Trp Arg Phe Ile Arg Ile Asp Thr Ala Cys Val Cys
        130                 135                 140

Val Leu Ser Arg Lys Ala Val Arg Glx
145                 150
```

<210> SEQ ID NO 33
<211> LENGTH: 414
<212> TYPE: DNA
<213> ORGANISM: Artificial Sequence
<220> FEATURE:
<223> OTHER INFORMATION: Description of Artificial Sequence: Gene

<400> SEQUENCE: 33

```
gaattccata tgaaccagga acaggttagc ccgctgcccg tggaactcga gagctcttcc      60
cacccgattt tccatcgtgg cgagttctcc gtgtgtgact ctgtctctgt atgggtaggc     120
gataaaacca ctgccactga tatcaaaggc aaagaggtga tggtgctggg agaagtaaac     180
attaacaact ctgtattcaa acagtacttc ttcgaaacta agtgccgtga cccgaacccg     240
gtagactctg ggtgtcgcgg catcgattct aaacactgga actcttactg caccactact     300
cacactttcg ttaaagcgtt gactatggat ggtaaacagg ctgcctggcg tttcatccgt     360
atcgatactg catgcgtgtg tgtactgtcc cgtaaagctg ttcgttaagg atcc           414
```

<210> SEQ ID NO 34
<211> LENGTH: 157
<212> TYPE: PRT
<213> ORGANISM: Artificial Sequence
<220> FEATURE:
<223> OTHER INFORMATION: Description of Artificial Sequence: Protein
      Sequence

<400> SEQUENCE: 34

```
Met Gly Ser Ser His His His His His His Ser Ser Gly Leu Val Pro
 1               5                  10                  15

Arg Gly Ser His Met Lys Asp Pro Lys Arg Leu Tyr Arg Ser Arg Lys
                20                  25                  30

Leu Pro Val Glu Leu Glu Ser Ser His Pro Ile Phe His Arg Gly
            35                  40                  45

Glu Phe Ser Val Cys Asp Ser Val Ser Val Trp Val Gly Asp Lys Thr
 50                  55                  60

Thr Ala Thr Asp Ile Lys Gly Lys Glu Val Met Val Leu Gly Glu Val
```

-continued

```
                65                   70                  75                  80
Asn Ile Asn Asn Ser Val Phe Lys Gln Tyr Phe Phe Glu Thr Lys Cys
                            85                  90                  95

Arg Asp Pro Asn Pro Val Asp Ser Gly Cys Arg Gly Ile Asp Ser Lys
                100                 105                 110

His Trp Asn Ser Tyr Cys Thr Thr Thr His Thr Phe Val Lys Ala Leu
            115                 120                 125

Thr Met Asp Gly Lys Gln Ala Ala Trp Arg Phe Ile Arg Ile Asp Thr
        130                 135                 140

Ala Cys Val Cys Val Leu Ser Arg Lys Ala Val Arg Glx
145                 150                 155
```

<210> SEQ ID NO 35
<211> LENGTH: 432
<212> TYPE: DNA
<213> ORGANISM: Artificial Sequence
<220> FEATURE:
<223> OTHER INFORMATION: Description of Artificial Sequence: Gene

<400> SEQUENCE: 35

```
gaattcccat ggcatatgaa agacccgaaa cgtctgtacc gttctcgtaa actgcccgtg      60
gaactcgaga gctcttccca cccgattttc catcgtggcg agttctccgt gtgtgactct     120
gtctctgtat gggtaggcga taaaaccact gccactgata tcaaaggcaa agaggtgatg     180
gtgctgggag aagtaaacat taacaactct gtattcaaac agtacttctt cgaaactaag     240
tgccgtgacc cgaacccggt agactctggg tgtcgcggca tcgattctaa acactggaac     300
tcttactgca ccactactca cactttcgtt aaagcgttga ctatggatgg taaacaggct     360
gcctggcgtt tcatccgtat cgatactgca tgcgtgtgtg tactgtcccg taaagctgtt     420
cgttaaggat cc                                                         432
```

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: bi-domain
      peptide
<221> NAME/KEY: MOD_RES
<222> LOCATION: (10)
<223> OTHER INFORMATION: bAla  beta Alanine

<400> SEQUENCE: 36

```
Leu Asn Gln Glu Gln Val Ser Pro Lys Ala Phe Ala Lys Leu Ala Ala
 1               5                   10                  15

Arg Leu Tyr Arg Lys Ala
            20
```

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Non
      functional plasmin substrate

<400> SEQUENCE: 37

```
Leu Ile Asn Met Lys Pro
 1               5
```